United States Patent
Miyazaki

(10) Patent No.: US 11,271,169 B2
(45) Date of Patent: Mar. 8, 2022

(54) NITROGEN-CONTAINING COMPOUND AND ORGANIC ELECTROLUMINESCENCE DEVICE INCLUDING THE SAME

(71) Applicant: SAMSUNG DISPLAY CO., LTD., Yongin-si (KR)

(72) Inventor: Yuuki Miyazaki, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 425 days.

(21) Appl. No.: 15/969,945

(22) Filed: May 3, 2018

(65) Prior Publication Data

US 2019/0067592 A1 Feb. 28, 2019

(30) Foreign Application Priority Data

Aug. 24, 2017 (KR) ........................ 10-2017-0107556

(51) Int. Cl.
| | |
|---|---|
| *H01L 51/00* | (2006.01) |
| *C07D 401/14* | (2006.01) |
| *C09K 11/06* | (2006.01) |
| *H01L 51/56* | (2006.01) |
| *H01L 51/50* | (2006.01) |

(52) U.S. Cl.
CPC ........ *H01L 51/0067* (2013.01); *C07D 401/14* (2013.01); *C09K 11/06* (2013.01); *H01L 51/0059* (2013.01); *H01L 51/0072* (2013.01); *H01L 51/0094* (2013.01); *C09K 2211/1018* (2013.01); *H01L 51/001* (2013.01); *H01L 51/5012* (2013.01); *H01L 51/56* (2013.01); *H01L 2251/558* (2013.01)

(58) Field of Classification Search
CPC ............ H01L 51/0067; H01L 51/0094; H01L 51/0059; H01L 51/0072; H01L 51/1018; H01L 51/56; H01L 51/558; H01L 51/001; H01L 51/5012; C07D 401/14; C09K 11/06
See application file for complete search history.

(56) References Cited

U.S. PATENT DOCUMENTS

| | | | |
|---|---|---|---|
| 8,173,274 B2 | 5/2012 | Lin et al. | |
| 8,643,268 B2 | 2/2014 | Ogiwara et al. | |
| 8,852,759 B2 | 10/2014 | Yokoyama et al. | |
| 9,818,949 B2 | 11/2017 | Yokoyama et al. | |
| 2014/0316134 A1 | 10/2014 | Stoessel et al. | |
| 2016/0172600 A1 | 6/2016 | MacDonald et al. | |
| 2016/0197286 A1 | 7/2016 | Kawamura et al. | |
| 2017/0018600 A1 | 1/2017 | Ito et al. | |
| 2018/0170914 A1* | 6/2018 | Miyata | ................. C07D 403/14 |

FOREIGN PATENT DOCUMENTS

| | | | | |
|---|---|---|---|---|
| CN | 105399696 A | | 3/2016 | |
| JP | 2016-33115 A | | 3/2016 | |
| JP | 6081473 B2 | | 2/2017 | |
| KR | 1020110120075 | * | 11/2011 | ............. C09K 11/06 |
| KR | 10-2013-0075949 A | | 7/2013 | |
| KR | 10-2013-0112850 A | | 10/2013 | |
| KR | 10-2013-0142967 A | | 12/2013 | |
| KR | 10-1366492 B1 | | 2/2014 | |
| KR | 10-2016-0035062 A | | 3/2016 | |
| KR | 10-2016-0080420 A | | 7/2016 | |
| KR | 10-2016-0101214 A | | 8/2016 | |
| KR | 10-1664122 B1 | | 10/2016 | |
| KR | 10-2017-0008358 A | | 1/2017 | |
| KR | 10-1769764 B1 | | 8/2017 | |
| KR | 101825381 B1 | * | 3/2018 | ........... C07D 487/00 |
| WO | WO 2011/155169 A1 | | 12/2011 | |
| WO | WO 2013/083216 A1 | | 6/2013 | |
| WO | WO 2015/016200 A1 | | 2/2015 | |
| WO | WO 2015/022835 A1 | | 2/2015 | |
| WO | WO 2016/017684 A1 | | 2/2016 | |

* cited by examiner

*Primary Examiner* — Robert S Jones, Jr.
(74) *Attorney, Agent, or Firm* — Lewis Roca Rothgerber Christie LLP

(57) ABSTRACT

A nitrogen-containing compound and an organic electroluminescence device, the compound being represented by the following Formula 1:

[Formula 1]

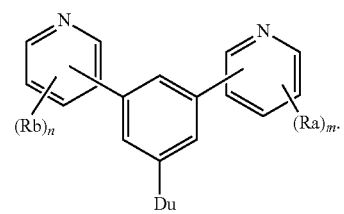

16 Claims, 1 Drawing Sheet

NITROGEN-CONTAINING COMPOUND AND ORGANIC ELECTROLUMINESCENCE DEVICE INCLUDING THE SAME

CROSS-REFERENCE TO THE RELATED APPLICATION

Korean Patent Application No. 10-2017-0107556, filed on Aug. 24, 2017, in the Korean Intellectual Property Office, and entitled: "Nitrogen-Containing Compound and Organic Electroluminescence Device Including the Same," is incorporated by reference herein in its entirety.

BACKGROUND

1. Field

Embodiments relate to a nitrogen-containing compound and an organic electroluminescence device including the same.

2. Description of the Related Art

Recently, the development of an organic electroluminescence display device as an image display device has been considered. Different from a liquid crystal display device, the organic electroluminescence display device is a self-luminescent display device in which holes and electrons injected from a first electrode and a second electrode recombine in an emission layer, and a light emission material including an organic compound in the emission layer emits light to attain display.

In the application of an organic electroluminescence device to a display device, the decrease of the driving voltage, and the increase of the emission efficiency and the life of the organic electroluminescence device may be desirable, and developments on materials for an organic electroluminescence device stably attaining the requirements may be considered.

SUMMARY

Embodiments are directed to a nitrogen-containing compound and an organic electroluminescence device including the same.

The embodiments may be realized by providing a nitrogen-containing compound represented by the following Formula 1:

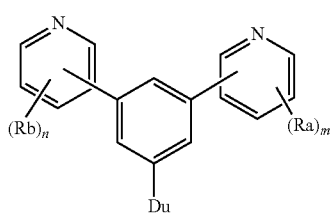

[Formula 1]

wherein, in Formula 1, Ra and Rb are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, m and n are each independently an integer of 0 to 4, and Du is a group represented by the following Formula 2-1 or Formula 2-2:

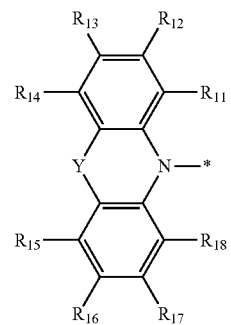

[Formula 2-1]

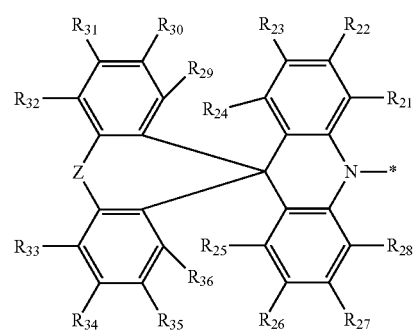

[Formula 2-2]

wherein, in Formula 2-1 and Formula 2-2, Y is $CR_1R_2$, or $NR_3$, Z is O, S, $CR_4R_5$, $NR_6$, or $SiR_7R_8$, $R_1$ to $R_8$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $R_1$ and $R_2$, $R_4$ and $R_5$, and $R_7$ and $R_8$ are separate or are combined with each other to form a ring, $R_{11}$ to $R_{18}$, and $R_{21}$ to $R_{36}$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and in $R_{11}$ to $R_{18}$, and $R_{21}$ to $R_{36}$, substituents of the substituted or unsubstituted alkyl group having 1 to 10 carbon atoms, the substituted or unsubstituted aryl group having 6 to 30 ring carbon atoms, and the substituted or unsubstituted heteroaryl group having 2 to 30 ring carbon atoms, are each independently a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms.

The compound represented by Formula 1 may be represented by one of the following Formula 1-1 to Formula 1-3:

[Formula 1-1]

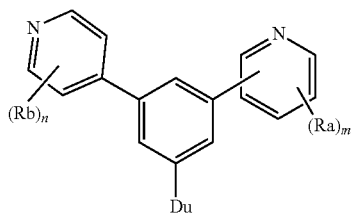

[Formula 1-2]

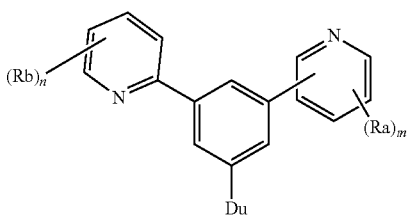

[Formula 1-3]

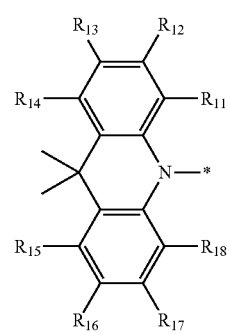

wherein, in Formula 1-1 to Formula 1-3, Du, Ra, Rb, m and n are defined the same those of Formula 1.

The nitrogen-containing compound represented by Formula 1 may be a material for emitting thermally activated delayed fluorescence.

The nitrogen-containing compound represented by Formula 1 may have an absolute value of a difference between a singlet energy level and a triplet energy level of 0.1 eV or less.

A triplet energy level of the nitrogen-containing compound represented by Formula 1 may be 2.7 eV or more.

Du may be a group represented by Formula 2-1, and the group represented by Formula 2-1 may be a group represented by one of the following Formula 2a to Formula 2c:

[Formula 2a]

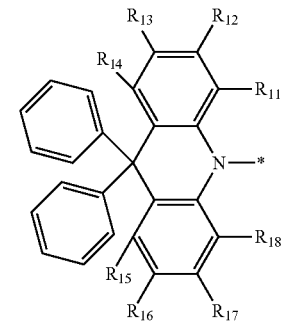

[Formula 2b]

[Formula 2c]

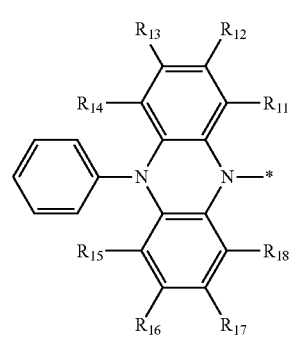

wherein, in Formula 2a to Formula 2c, $R_{11}$ to $R_{18}$ are defined the same as those of Formula 2-1.

Du may be a group represented by Formula 2-2, and the group represented by Formula 2-2 may be a group represented by one of the following Formula 2d to Formula 2i:

[Formula 2d]

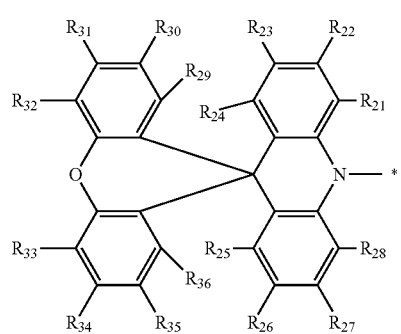

[Formula 2e]

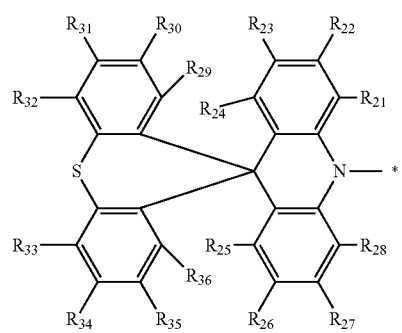

[Formula 2f]

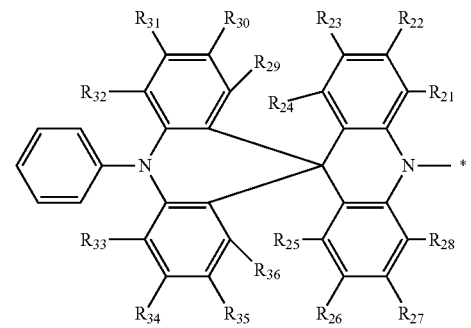

[Formula 2g]

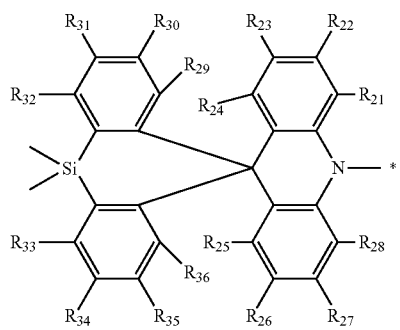

[Formula 2h]

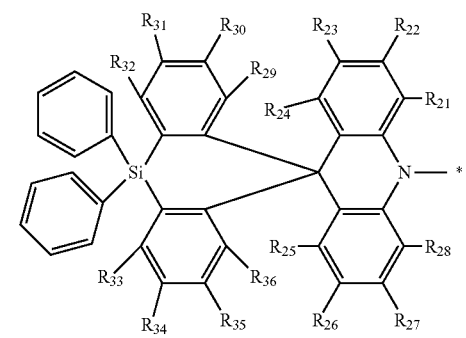

[Formula 2i]

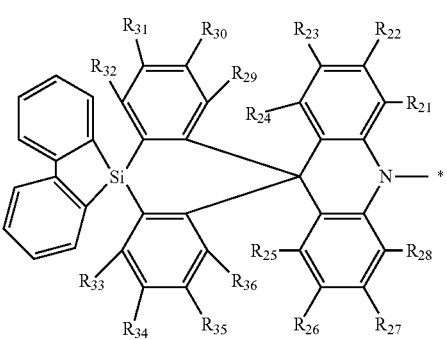

wherein, in Formula 2d to Formula 2i, $R_{21}$ to $R_{36}$ are defined the same as those of Formula 2-2.

In Formula 2-1 and Formula 2-2, $R_{11}$ to $R_{18}$, and $R_{21}$ to $R_{36}$ may each independently be a hydrogen atom, a methyl group, a t-butyl group, or an unsubstituted phenyl group.

The nitrogen-containing compound represented by Formula 1 may be a compound of the following Compound Group 1:

[Compound Group 1]

1

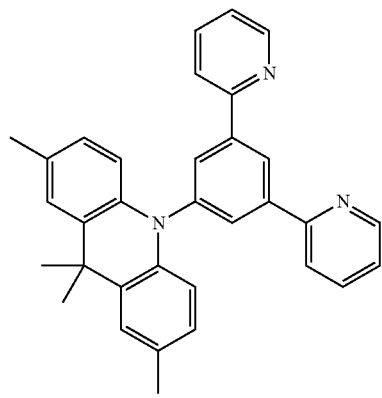

2

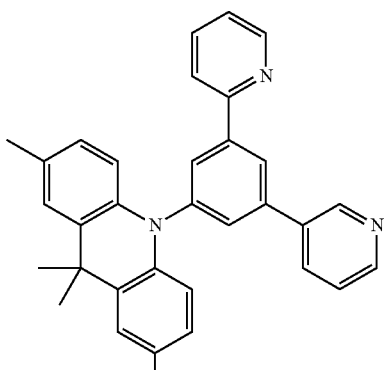

3

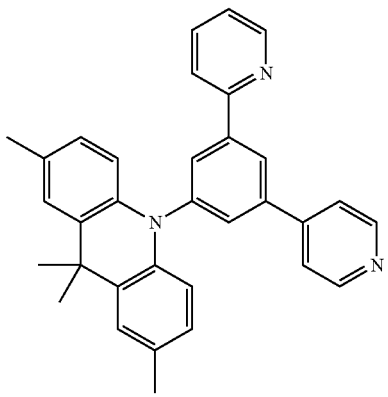

4

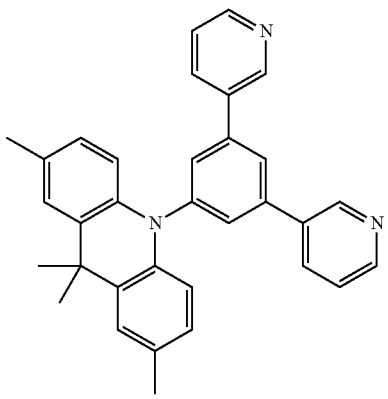

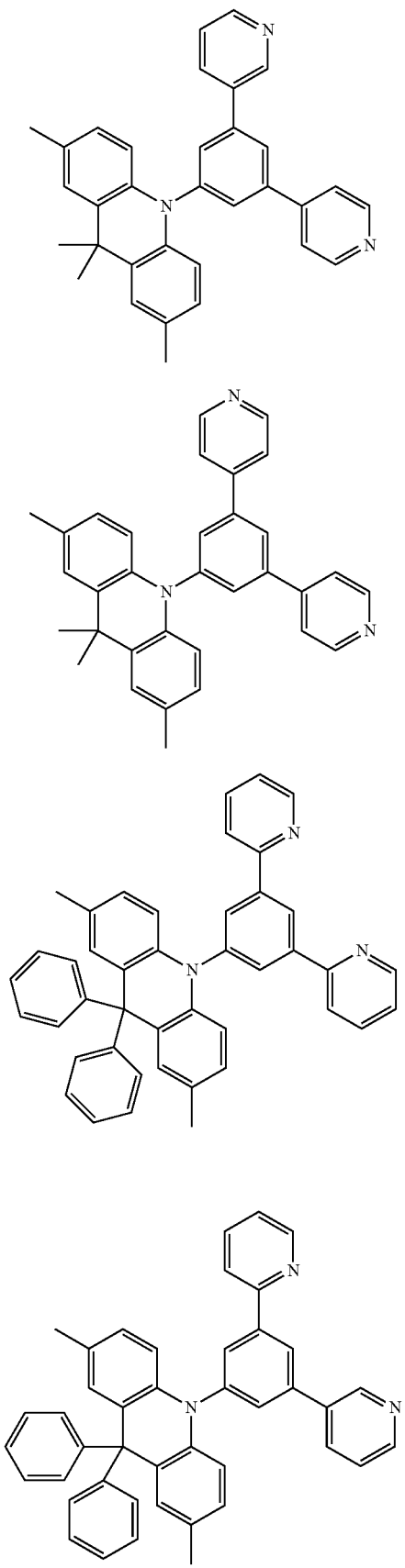
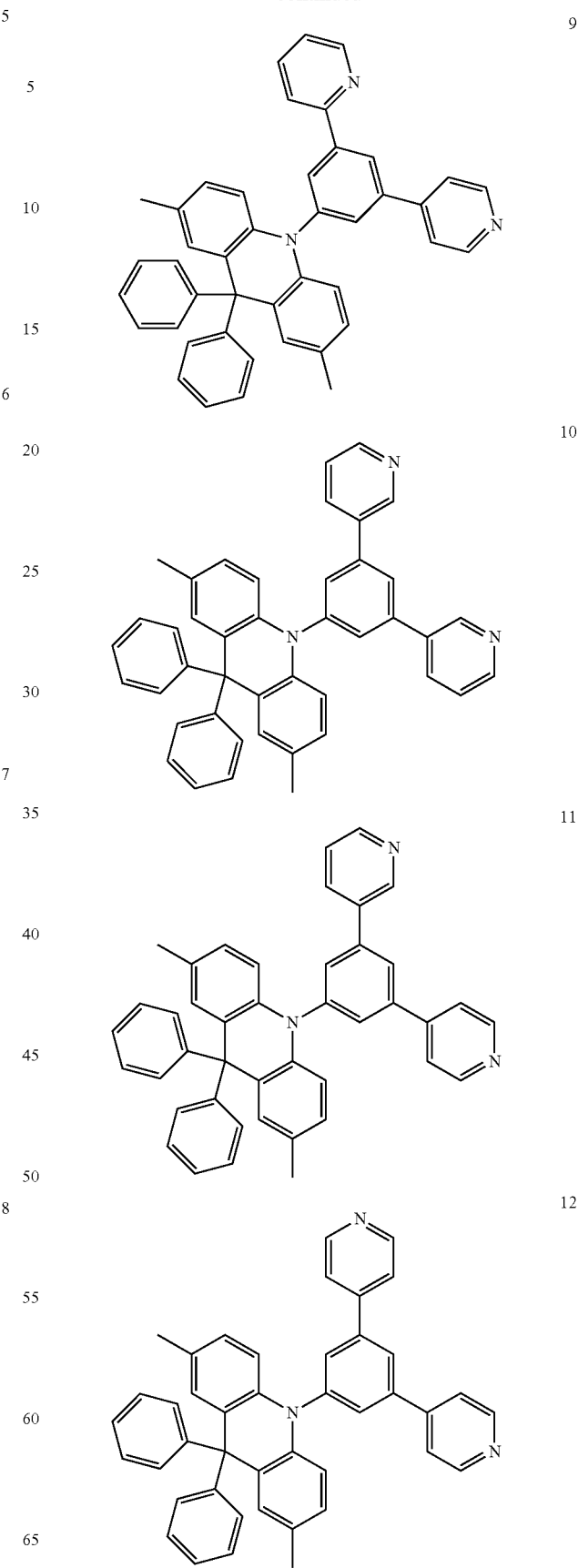

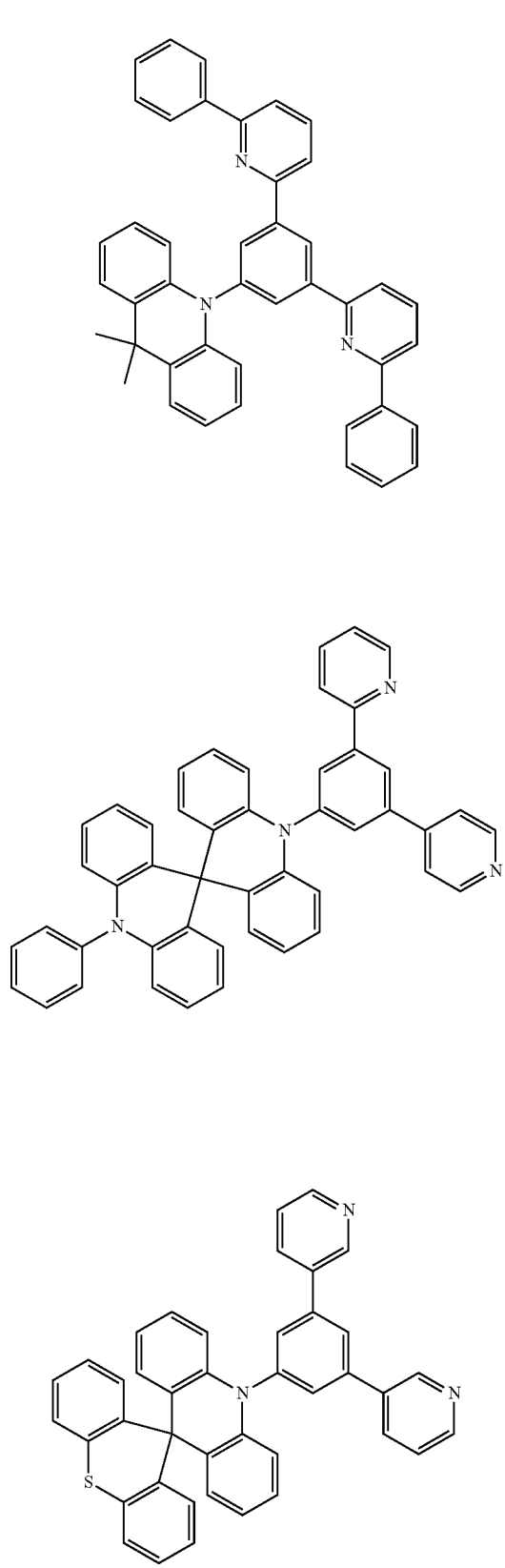
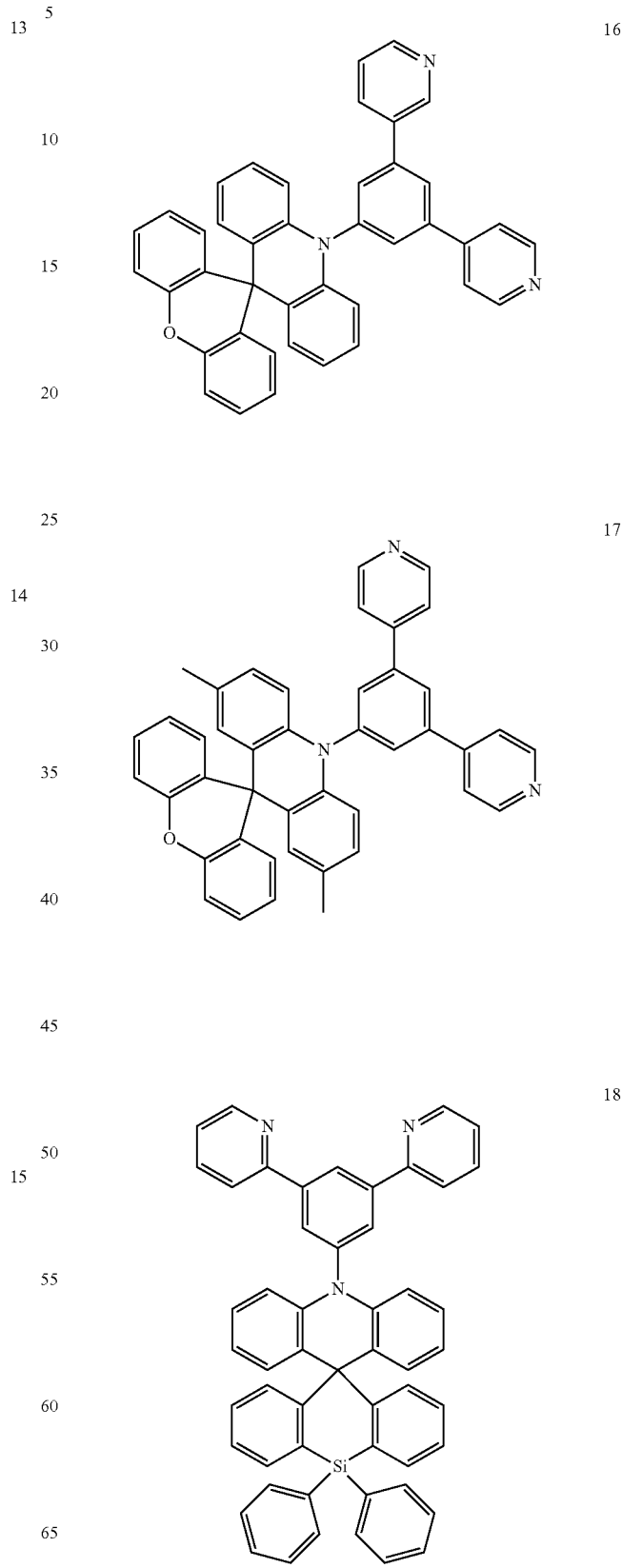

19

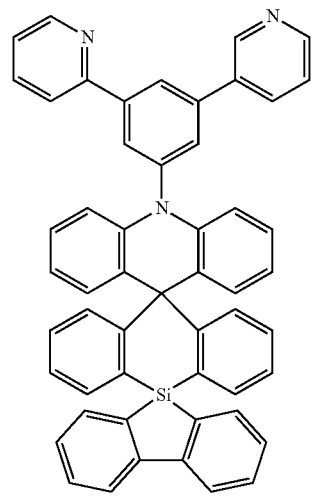

20

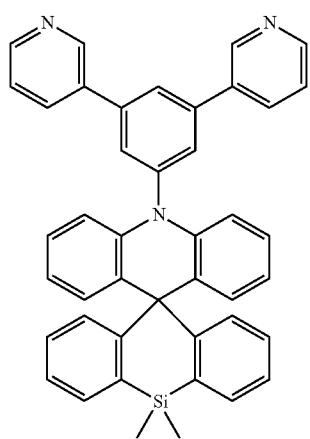

21

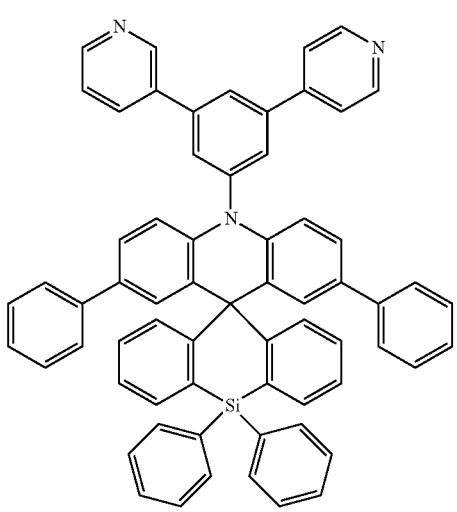

22

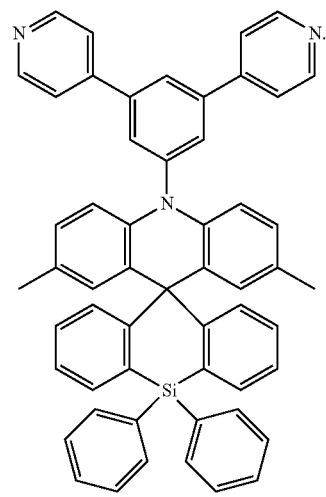

The embodiments may be realized by providing an organic electroluminescence device including a first electrode; a hole transport region disposed on the first electrode; an emission layer disposed on the hole transport region; an electron transport region disposed on the emission layer; and a second electrode disposed on the electron transport region, wherein the first electrode and the second electrode may each independently include at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more thereof, a mixture of two or more thereof, or an oxide thereof, and wherein the emission layer includes a nitrogen-containing compound represented by the following Formula 1:

[Formula 1]

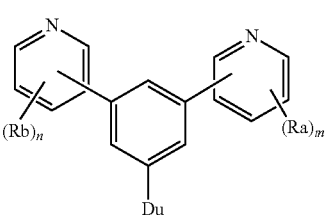

wherein, in Formula 1, Ra and Rb are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, m and n are each independently an integer of 0 to 4, and Du is a group represented by the following Formula 2-1 or Formula 2-2:

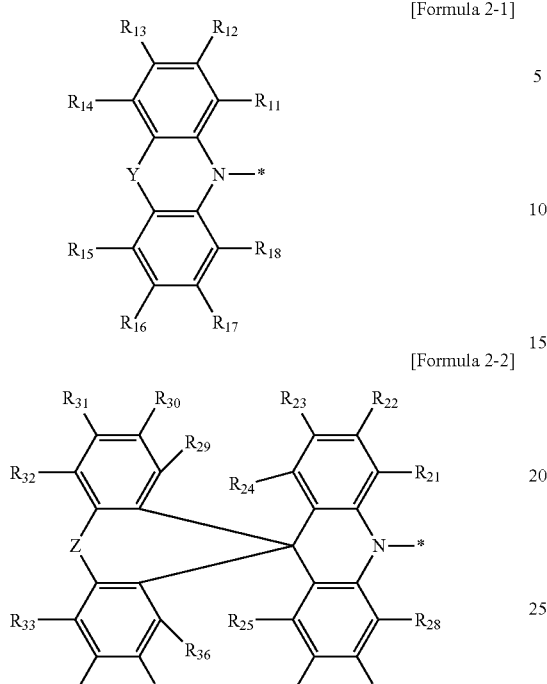

[Formula 2-1]

[Formula 2-2]

wherein, in Formula 2-1 and Formula 2-2, Y is $CR_1R_2$, or $NR_3$, Z is O, S, $CR_4R_5$, $NR_6$, or $SiR_7R_8$, $R_1$ to $R_8$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $R_1$ and $R_2$, $R_4$ and $R_5$, and $R_7$ and $R_8$ are separate or are combined with each other to form a ring, $R_{11}$ to $R_{18}$, and $R_{21}$ to $R_{36}$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and in $R_{11}$ to $R_{18}$, and $R_{21}$ to $R_{36}$, substituents of the substituted or unsubstituted alkyl group having 1 to 10 carbon atoms, the substituted or unsubstituted aryl group having 6 to 30 ring carbon atoms, and the substituted or unsubstituted heteroaryl group having 2 to 30 ring carbon atoms, are each independently a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms.

The emission layer may emit delayed fluorescence.

The emission layer may be a delayed fluorescence emission layer including a host and a dopant, and the dopant may include the nitrogen-containing compound represented by Formula 1.

The emission layer may be a thermally activated delayed fluorescence emission layer emitting blue light.

The compound represented by Formula 1 may be represented by one of the following Formula 1-1 to Formula 1-3:

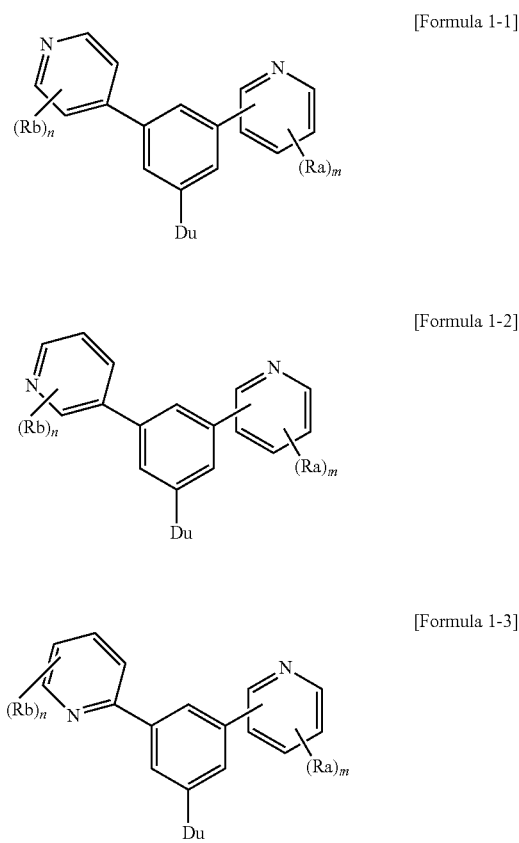

[Formula 1-1]

[Formula 1-2]

[Formula 1-3]

wherein, in Formula 1-1 to Formula 1-3, Du, Ra, Rb, m and n are defined the same those of Formula 1.

Du of Formula 1 may be a group represented by one of the following Formula 2a to Formula 2i:

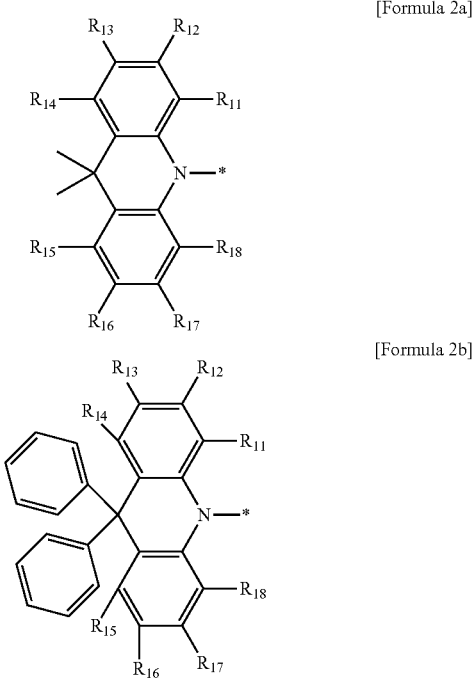

[Formula 2a]

[Formula 2b]

[Formula 2c] 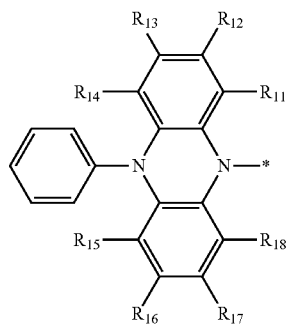
[Formula 2d] 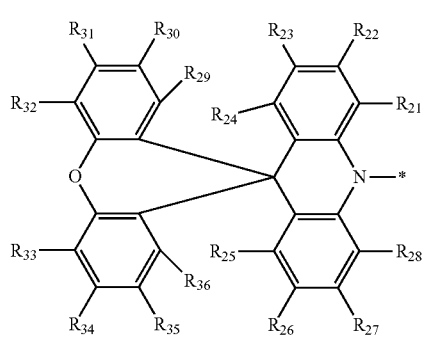
[Formula 2e] 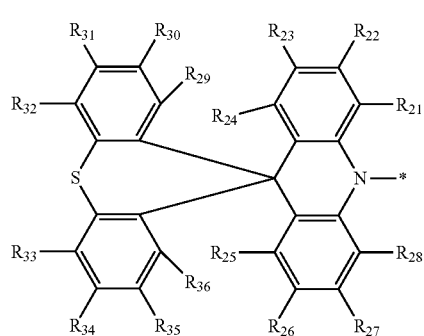
[Formula 2f] 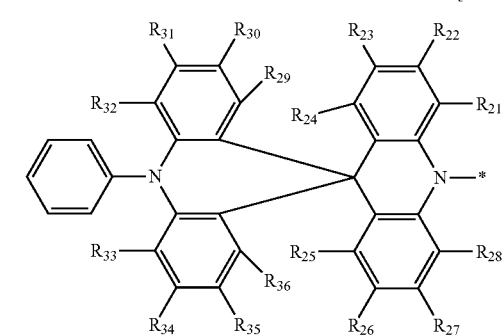
[Formula 2g] 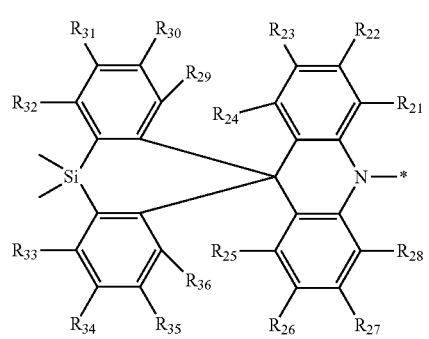
[Formula 2h] 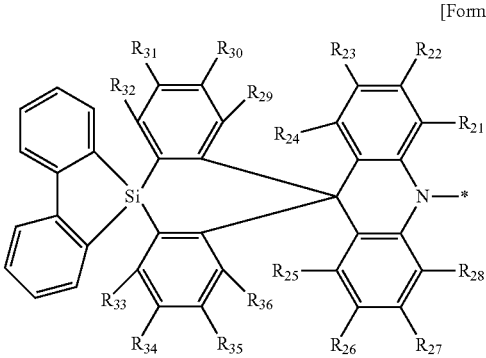
[Formula 2i] 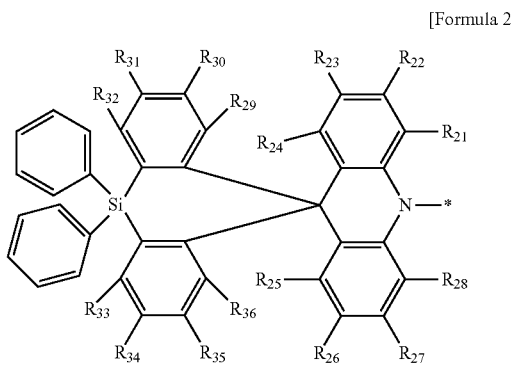
wherein, in Formula 2a to Formula 2i, $R_{11}$ to $R_{18}$, and $R_{21}$ to $R_{36}$ are defined the same as those of Formula 2-1 and Formula 2-2.
The nitrogen-containing compound represented by Formula 1 may be a compound of the following Compound Group 1:

[Compound Group 1]
1
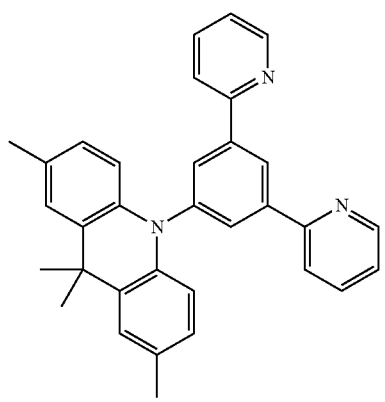
2
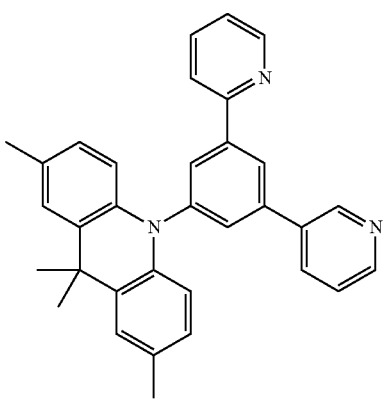
3
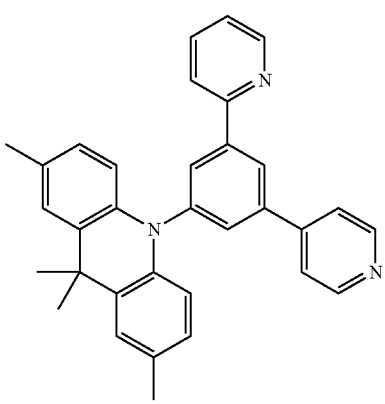
4
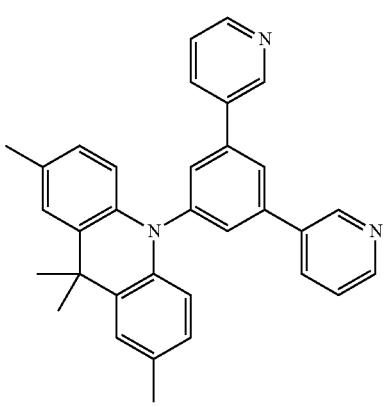
-continued
5
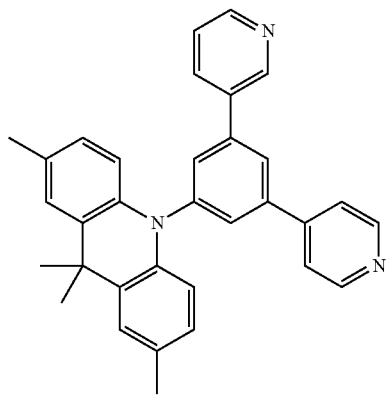
6
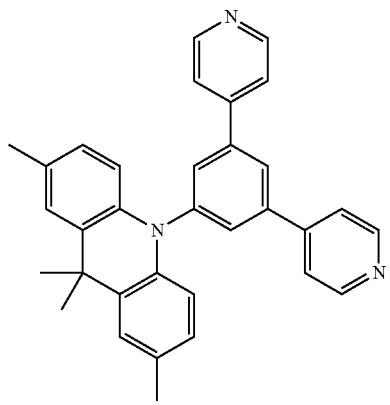
7
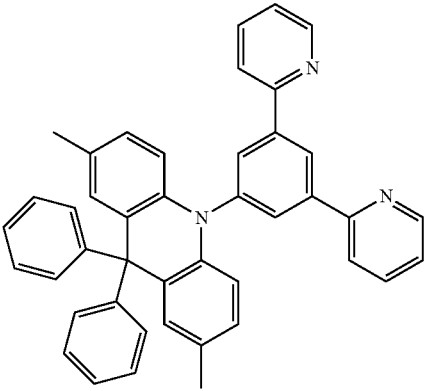
8
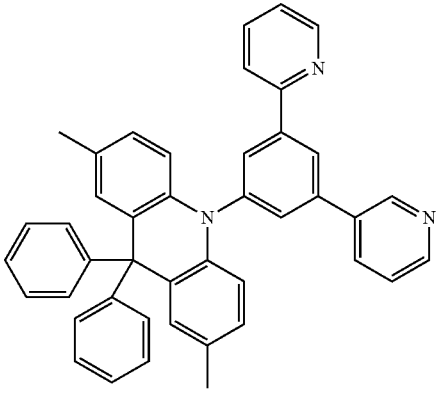

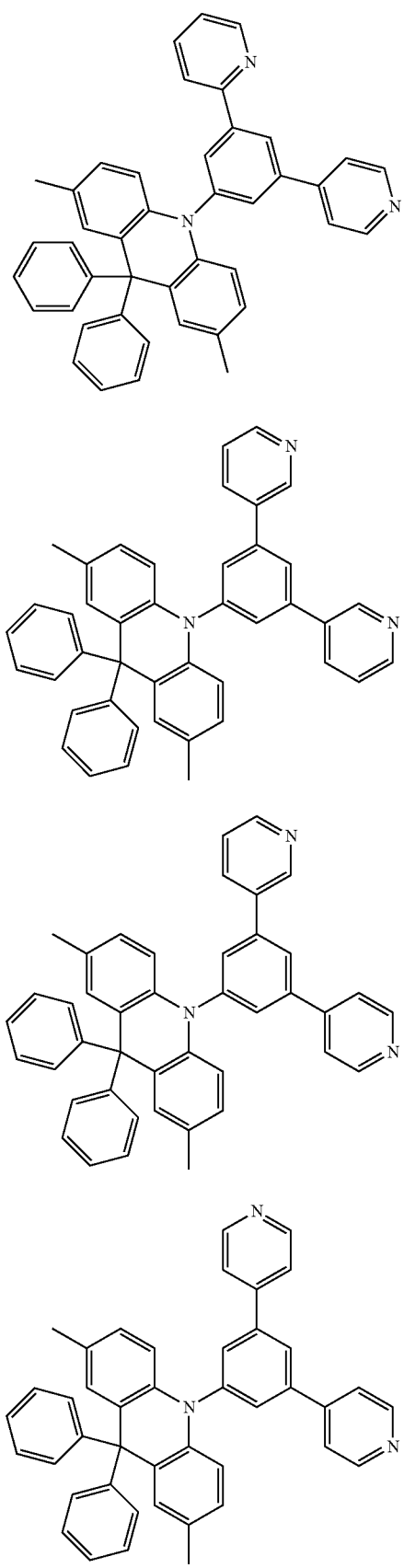
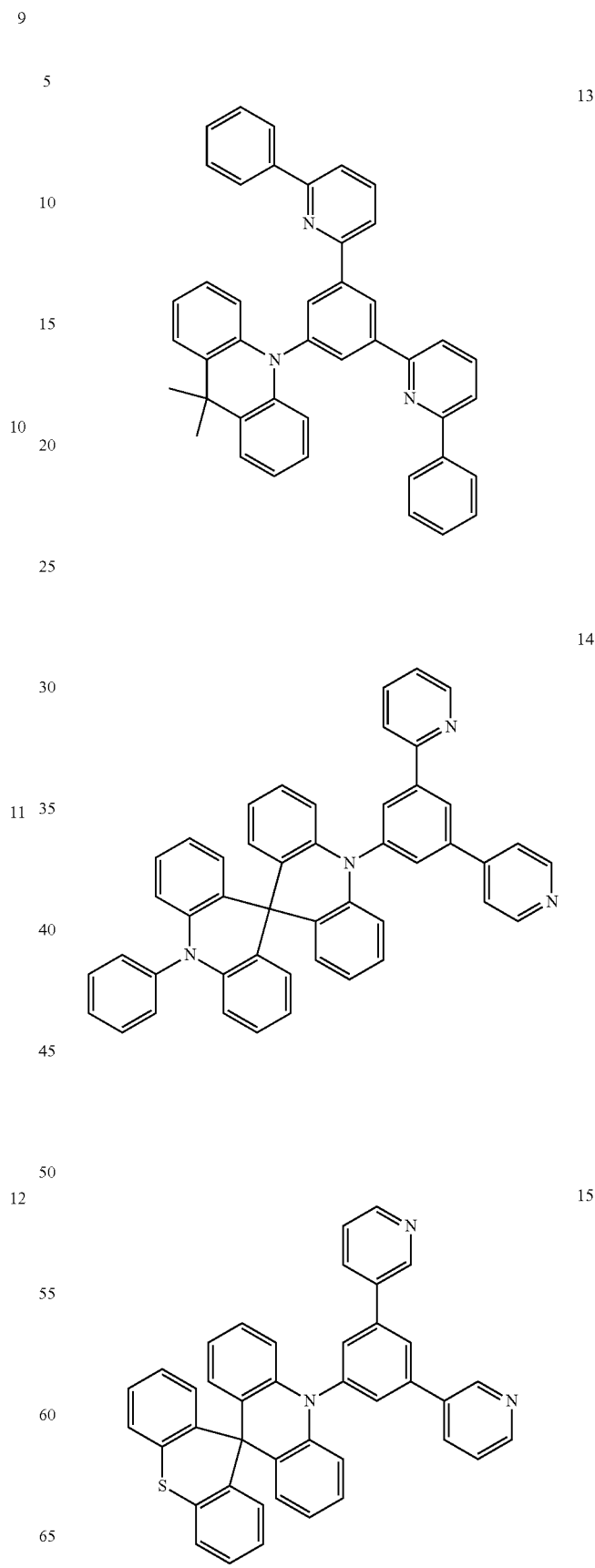

16
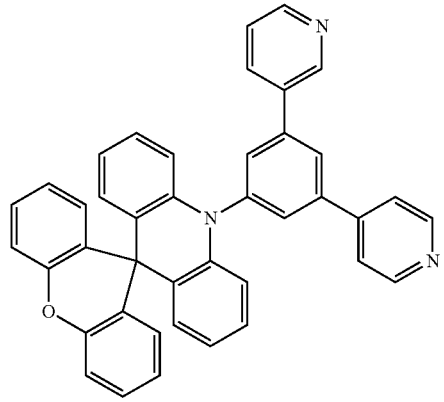
17
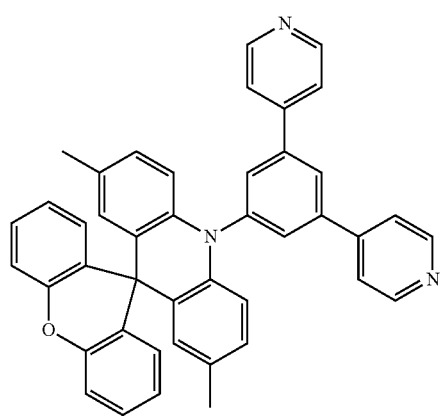
18
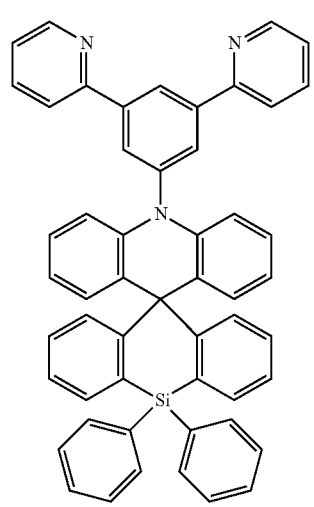
19
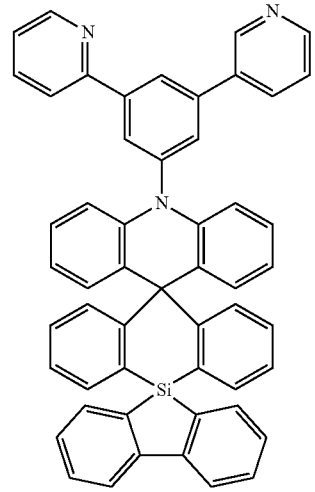
20
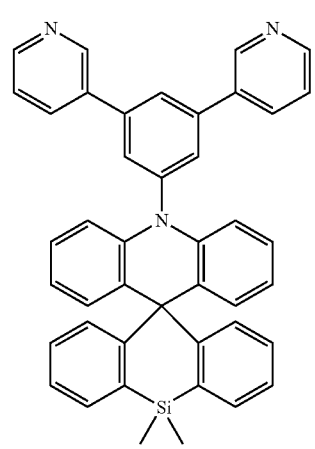
21
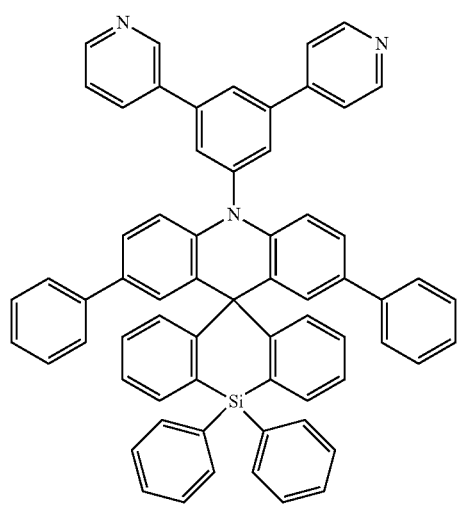

-continued

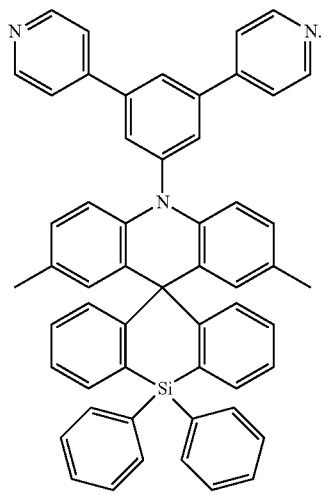

22

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
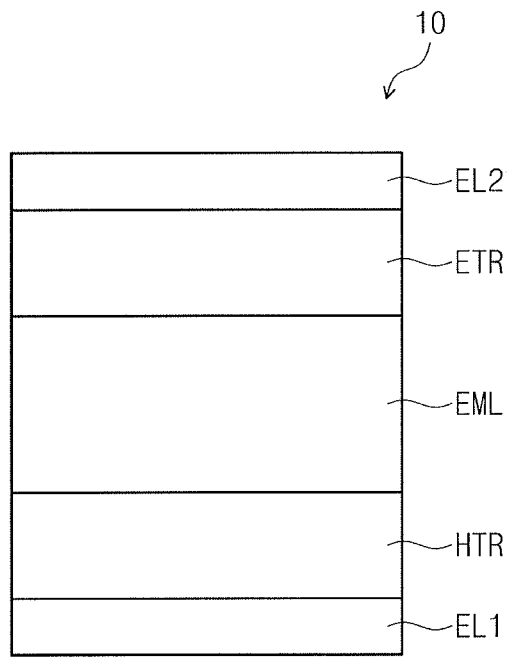
FIGS. 1 and 2 illustrate cross-sectional views of organic electroluminescence devices according to exemplary embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. Thus, a first element could be termed a second element without departing from the teachings herein. Similarly, a second element could be termed a first element. As used herein, the singular forms are intended to include the plural forms as well, unless the context clearly indicates otherwise.

It will be further understood that the terms "includes," "including," "comprises," and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being 'on' another part, it can be directly on the other part, or intervening layers may also be present. As used herein, the term "or" is not an exclusive term, e.g., "or" would mean the same as "and/or."

In the description, -* means a connecting position.

In the description, the term "substituted or unsubstituted" corresponds to substituted or unsubstituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocyclic group. In addition, each of the substituents may be substituted or unsubstituted. For example, a biphenyl group may be interpreted as an aryl group or a phenyl group substituted with a phenyl group.

In the description, the description of forming a ring via the combination with an adjacent group, may mean forming a substituted or unsubstituted hydrocarbon ring, or substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic or polycyclic. In addition, the ring formed via the combination with an adjacent group may be combined with another ring to form a spiro structure.

In the description, the terms "an adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the halogen atom may include a fluorine atom, a chlorine atom, a bromine atom and an iodine atom.

In the description, the alkyl may be a linear, branched or cyclic type. The carbon number of the alkyl may be from 1 to 50, from 1 to 30, from 1 to 20, from 1 to 10, or from 1 to 6. The alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the aryl group means an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the description, the fluorenyl group may be substituted, and two substituents may be combined with each other to form a spiro structure.

In the description, the heteroaryl may be a heteroaryl including at least one of O, N, P, Si or S as a heteroatom. The carbon number for forming a ring of the heteroaryl may be 2 to 30, or 2 to 20. The heteroaryl may be monocyclic heteroaryl or polycyclic heteroaryl. Examples of the polycyclic heteroaryl may have dicyclic or tricyclic structure. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzosilole, dibenzofuranyl, etc., without limitation.

In the description, a silyl group includes an alkylsilyl group and an arylsilyl group. Examples of the silyl group may include a trimethyl silyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the description, a boron group includes an alkyl boron group and an aryl boron group. Examples of the boron group may include a trimethyl boron group, a triethylboron group, a t-butyldimethylboron group, a triphenylboron group, a diphenylboron group, a phenylboron group, etc., without limitation.

In the description, an alkenyl group may be a linear or a branched chain. The carbon number is not specifically limited, but may be from 2 to 30, from 2 to 20, or from 2 to 10. Examples of the alkenyl group may include a vinyl group, a 1-butenyl group, a 1-pentenyl group, a 1,3-butadienyl aryl group, a styrenyl group, a styryl vinyl group, etc., without limitation.

In the description, the carbon number of the amine group is not specifically limited, and may be 1 to 30. The amine group may include an alkylamine group and an arylamine group. Examples of the amine group may include a methylamine group, a dimethylamine group, a phenylamine group, a naphthylamine group, a 9-methyl-anthracenylamine group, a triphenylamine group, etc., without limitation.

Hereinafter, a nitrogen-containing compound according to an embodiment will be explained.

A nitrogen-containing compound according to an embodiment may be represented by, e.g., the following Formula 1.

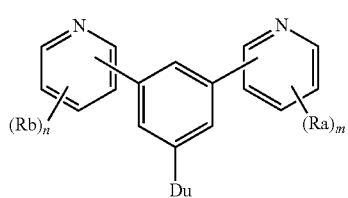

[Formula 1]

In Formula 1, Ra and Rb may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In Formula 1, m and n may be each independently an integer of 0 to 4. For example, case where m or n is 0 may mean that the nitrogen-containing compound represented by Formula 1 is not substituted with Ra or Rb, and would be the same as a case where m is 1 and Ra is hydrogen, n is 1 and Rb is hydrogen, etc.

In Formula 1, Du may be, e.g., a group represented by the following Formula 2-1 or Formula 2-2.

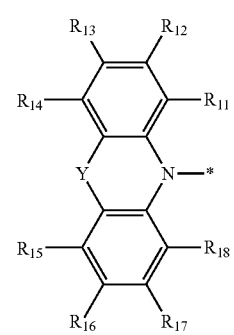

[Formula 2-1]

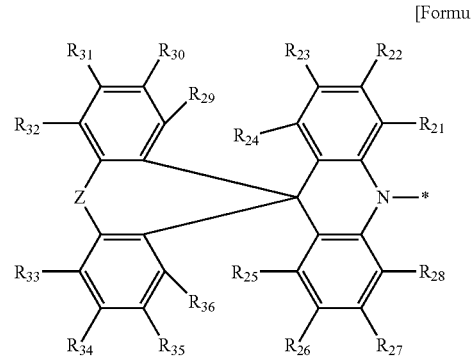

[Formula 2-2]

In Formulae 2-1 and 2-2, Y may be, e.g., $CR_1R_2$, or $NR_3$, Z may be, e.g., O, S, $CR_4R_5$, $NR_6$, or $SiR_7R_8$. $R_1$ to $R_8$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_1$ and $R_2$, $R_4$ and $R_5$, and $R_7$ and $R_8$ may be separate or may each independently combined with each other to form a ring.

$R_{11}$ to $R_{18}$ and $R_{21}$ to $R_{36}$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In $R_{11}$ to $R_{18}$ and $R_{21}$ to $R_{36}$, substituents of the substituted or unsubstituted alkyl group having 1 to 10 carbon atoms, the substituted or unsubstituted aryl group having 6 to 30 ring carbon atoms, and the substituted or unsubstituted heteroaryl group having 2 to 30 ring carbon atoms may each independently be or include, e.g., a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms.

In an implementation, in the nitrogen-containing compound of an embodiment, represented by Formula 1, Ra and Rb may be the same. In an implementation, Ra and Rb may be different from each other. For example, Ra and Rb may each independently be or include, e.g., a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, substituents of the substituted or unsubstituted alkyl group having 1 to 10 carbon atoms, the substituted or unsubstituted aryl group having 6 to 30 ring carbon atoms, or the substituted or unsubstituted heteroaryl group having 2 to 30 ring carbon atoms may be or may include, e.g., a deuterium atom, a halogen atom, a cyano group, an unsubstituted alkyl group having 1 to 10 carbon atoms, an unsubstituted aryl group having 6 to 30 ring carbon atoms, or an unsubstituted heteroaryl group having 2 to 30 ring carbon atoms. In an implementation, Ra and Rb may each be an unsubstituted phenyl group.

In an implementation, if m is an integer of 2 or more, the plurality of Ra groups may be the same or different. In an implementation, if n is an integer of 2 or more, the plurality of Rb groups may be the same or different.

In an implementation, m and n may be 0. If m and n are 0, in the nitrogen-containing compound, represented by Formula 1, a pyridine group may be an unsubstituted pyridine group. In an implementation, m and n may be 1, and Ra and Rb may be unsubstituted phenyl groups.

The nitrogen-containing compound of an embodiment, represented by Formula 1 may include two pyridine groups. The nitrogen-containing compound of an embodiment, represented by Formula 1 may include Du (which is an electron donor) and a pyridine group (which is an electron acceptor).

Two pyridine groups and Du may be disposed respectively at positions 1, 3 and 5 of a benzene ring which corresponds to a linker. In the nitrogen-containing compound of an embodiment, two pyridine groups and a polycyclic group (which is an acridine derivative represented by Du) may be bonded to meta positions from each other with a benzene ring as a linker.

In an implementation, the compound represented by Formula 1 may be represented by one of the following Formula 1-1 to Formula 1-3.

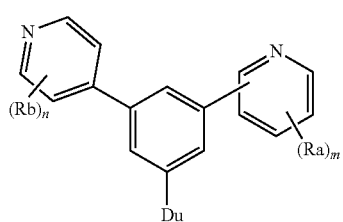

[Formula 1-1]

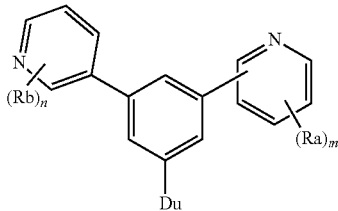

[Formula 1-2]

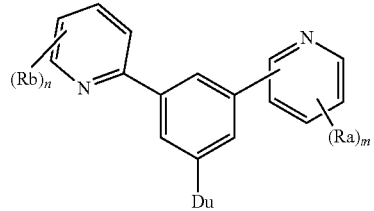

[Formula 1-3]

In Formula 1-1 to Formula 1-3, Du, Ra, Rb, m and n are the same as defined in Formula 1. Meanwhile, Formula 1-1 to Formula 1-3 are examples with different bonding positions of the pyridine groups bonded to the benzene ring which is a linker.

In Formula 2-1, Y may be, e.g., $CR_1R_2$. $R_1$ and $R_2$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_1$ and $R_2$ may be separate or may be combined with each other to form a ring. In an implementation, $R_1$ and $R_2$ may each independently be or include, e.g., a substituted or unsubstituted alkyl group having 1 to 10 carbon atoms or a substituted or unsubstituted aryl group having 6 to 30 ring carbon atoms. In an implementation, $R_1$ and $R_2$ may each independently be, e.g., a methyl group or an unsubstituted phenyl group.

In an implementation, in Formula 2-1, Y may be, e.g., $NR_3$, and $R_3$ may be or may include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_3$ may be, e.g., an unsubstituted phenyl group.

In Formula 2-1, $R_{11}$ to $R_{18}$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, in Formula 2-1, $R_{11}$ to $R_{18}$ may not form a ring via the combination with an adjacent substituent.

In an implementation, in $R_{11}$ to $R_{18}$ of Formula 2-1, an amine group may be excluded from the substituent of "substituted or unsubstituted". For example, in $R_{11}$ to $R_{18}$ of Formula 2-1, an arylamine group may be excluded from the substituent of "substituted or unsubstituted". In an implementation, $R_{11}$ to $R_{18}$ of Formula 2-1, may each independently include, e.g., a hydrogen atom, a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms.

In an implementation, in Formula 2-1, $R_1$ to $R_{18}$ may each independently be or include, e.g., a hydrogen atom, or a substituted or unsubstituted alkyl group having 1 to 10 carbon atoms. For example, $R_{11}$ to $R_{18}$ may each independently be a hydrogen atom or a methyl group.

In an implementation, in Formula 2-1, one of $R_{11}$ to $R_{14}$ may be a methyl group, and the remainder thereof may be hydrogen atoms. In an implementation, one of $R_{15}$ to $R_{18}$ may be a methyl group, and the remainder thereof may be hydrogen atoms. In an implementation, in Formula 2-1, $R_{13}$ and $R_{16}$ among $R_{11}$ to $R_{18}$ may be methyl groups, and the remainder thereof may be hydrogen atoms.

In an implementation, the group represented by Formula 2-1 may be a group represented by one of the following Formula 2a to Formula 2c.

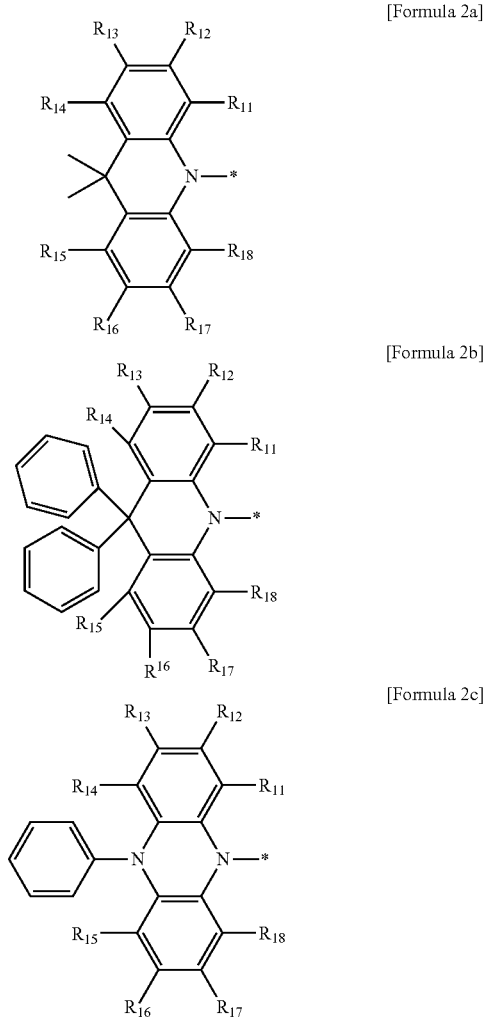

[Formula 2a]

[Formula 2b]

[Formula 2c]

In Formula 2a to Formula 2c, the same explanation on $R_{11}$ to $R_{18}$ of Formula 2-1 may be applied to that on $R_{11}$ to $R_{18}$.

In the nitrogen-containing compound of an embodiment, represented by Formula 1, Du may be, e.g., a group represented by Formula 2-2, and in Formula 2-2, Z may be, e.g., O, S, $CR_4R_5$, $NR_6$, or $SiR_7R_8$.

Z may be, e.g., $CR_4R_5$, and $R_4$ and $R_5$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_4$ and $R_5$ may be separate or may be combined with each other to form a ring. In an implementation, $R_4$ and $R_5$ may each independently be or include, e.g., a substituted or unsubstituted alkyl group having 1 to 10 carbon atoms or a substituted or unsubstituted aryl group having 6 to 30 carbon atoms. In an implementation, $R_4$ and $R_5$ may each independently be, e.g., a methyl group or an unsubstituted phenyl group.

Z may be, e.g., $SiR_7R_8$, and $R_7$ and $R_8$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_7$ and $R_8$ may be separate or may be combined with each other to form a ring. In an implementation, $R_7$ and $R_8$ may each independently be, e.g., a substituted or unsubstituted alkyl group having 1 to 10 carbon atoms, or a substituted or unsubstituted aryl group having 6 to 30 ring carbon atoms. In an implementation, $R_7$ and $R_8$ may each independently be, e.g., a methyl group or an unsubstituted phenyl group.

In an implementation, in Formula 2-2, Z may be, e.g., $NR_6$, and $R_6$ may be, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_6$ may be, e.g., an unsubstituted phenyl group.

In Formula 2-2, $R_{21}$ to $R_{28}$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_{21}$ to $R_{28}$ may not form a ring via the combination with an adjacent connecting group.

In an implementation, in $R_{21}$ to $R_{28}$ of Formula 2-2, an amine group may be excluded from the substituent of "substituted or unsubstituted". In an implementation, in $R_{21}$ to $R_{28}$, an arylamine group may be excluded from the substituent of "substituted or unsubstituted". In an implementation, $R_{21}$ to $R_{28}$ of Formula 2-2, may each independently be or include, e.g., a hydrogen atom, a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms.

In an implementation, $R_{21}$ to $R_{28}$ may each independently be or include, e.g., a hydrogen atom, a methyl group, a tert-butyl group, or an unsubstituted phenyl group. In an implementation, one of $R_{21}$ to $R_{24}$ of Formula 2-2 may be a methyl group and the remainder thereof may be hydrogen atoms. In an implementation, one of $R_{25}$ to $R_{28}$ may be a methyl group and the remainder thereof may be hydrogen atoms. In an implementation, in Formula 2-2, $R_{21}$ to $R_{28}$ may be hydrogen atoms. In an implementation, one of $R_{21}$ to $R_{24}$ of Formula 2-2 may be an unsubstituted phenyl group and the remainder thereof may be hydrogen atoms. In an implementation, one of $R_{25}$ to $R_{28}$ may be an unsubstituted phenyl group and the remainder thereof may be hydrogen atoms.

In an implementation, $R_{29}$ to $R_{36}$ of Formula 2-2 may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_{29}$ to $R_{36}$ may not form a ring via the combination with an adjacent connecting group.

In an implementation, in $R_{29}$ to $R_{36}$ of Formula 2-2, an amine group may be excluded from the substituent of "substituted or unsubstituted". In an implementation, in $R_{29}$ to $R_{36}$ of Formula 2-2, an arylamine group is excluded from the substituent of "substituted or unsubstituted". In an implementation, $R_{29}$ to $R_{36}$ of Formula 2-2 may each independently be, e.g., a hydrogen atom, a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms. In an implementation, $R_{29}$ to $R_{36}$ may be hydrogen atoms.

In an implementation, the group represented by Formula 2-2 may be, e.g., a group represented by one of the following Formula 2d to Formula 2i.

[Formula 2d]

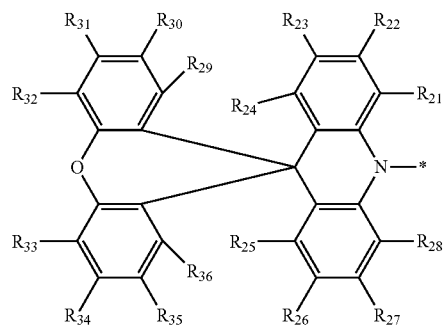

[Formula 2e]

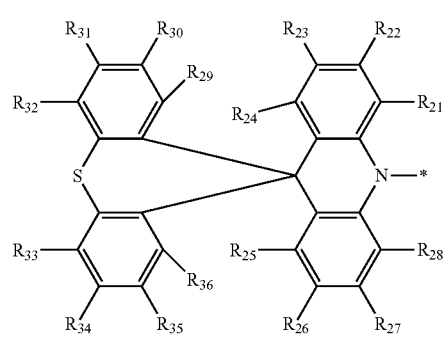

[Formula 2f]

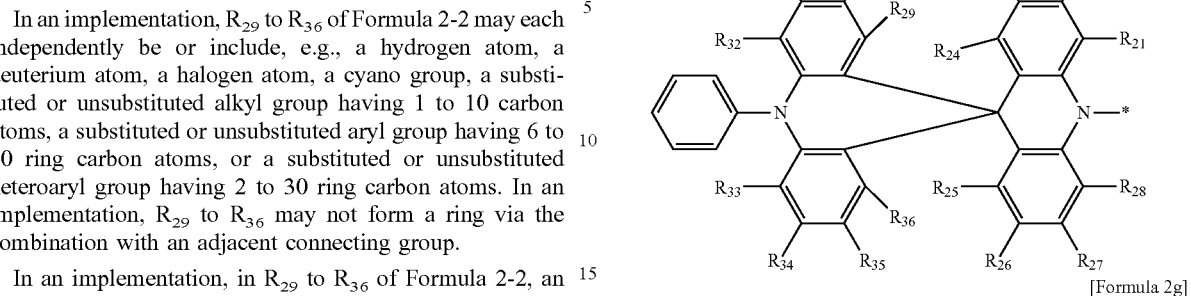

[Formula 2g]

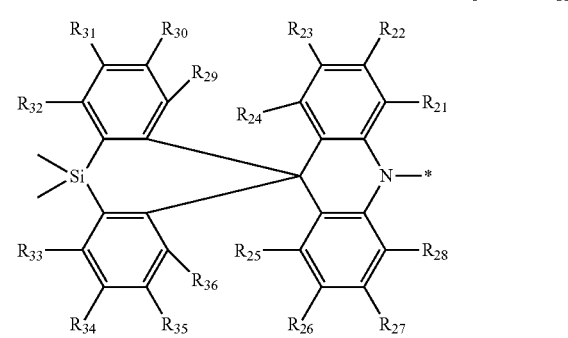

[Formula 2h]

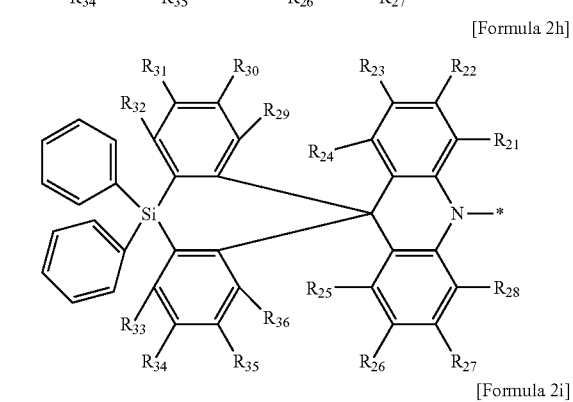

[Formula 2i]

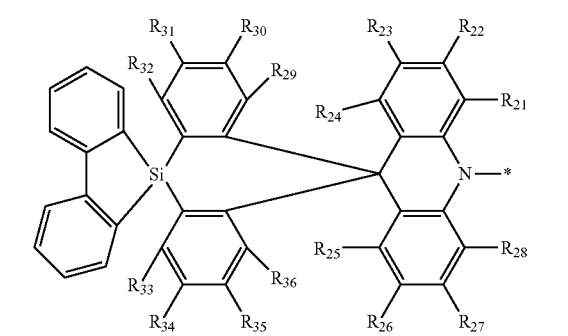

In Formula 2d to Formula 2i, the same explanation on $R_{21}$ to $R_{36}$ of Formula 2-2 may be applied to that of $R_{21}$ to $R_{36}$.

The nitrogen-containing compound of an embodiment, represented by Formula 1 may be a material for emitting delayed fluorescence. The nitrogen-containing compound of an embodiment may be a material for emitting thermally activated delayed fluorescence.

The nitrogen-containing compound, represented by Formula 1 of an embodiment may have an absolute value (Est) of a difference between a singlet energy level (S1) and a triplet energy level (T1) of about 0.1 eV or less. For example, a relation of S1−T1≤0.1 eV may be satisfied.

The triplet energy level (T1) of the nitrogen-containing compound, represented by Formula 1 may be about 2.7 eV or more. Meanwhile, a T1 energy level which is the triplet energy level may be calculated by a quantum chemical calculation method with the conditions of B3LYP/6-31G(d).

For example, the nitrogen-containing compound, represented by Formula 1 may have a high triplet energy level value and a small difference between a singlet energy level (S1) and a triplet energy level (T1), and may be used as a material for emitting thermally activated delayed fluorescence. For example, the nitrogen-containing compound, represented by Formula 1 may be used as a blue emitting material which emits thermally activated delayed fluorescence.

In an implementation, the nitrogen-containing compound of an embodiment, represented by Formula 1 may be, e.g., a compound of the following Compound Group 1.

[Compound Group 1]

1
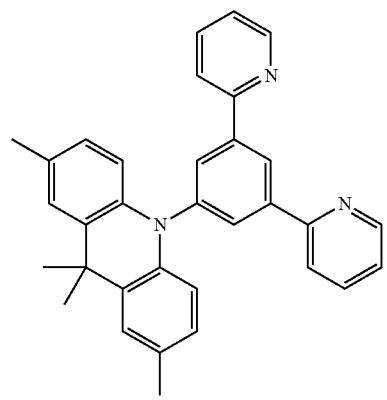

2
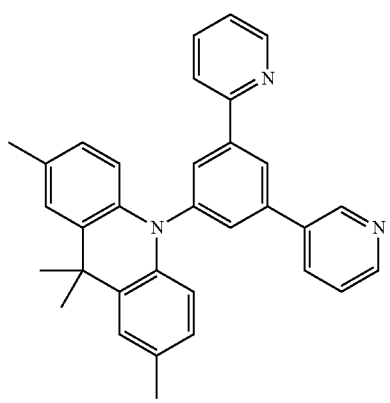

-continued

3
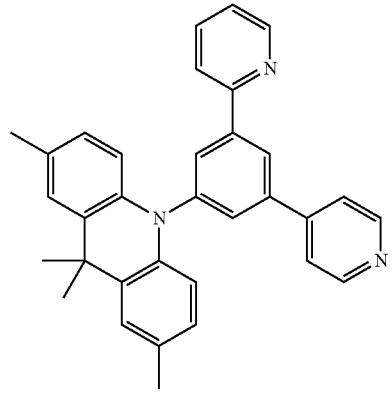

4
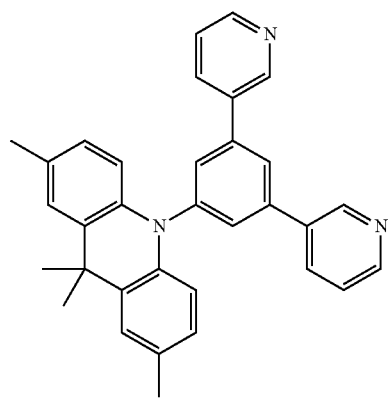

5
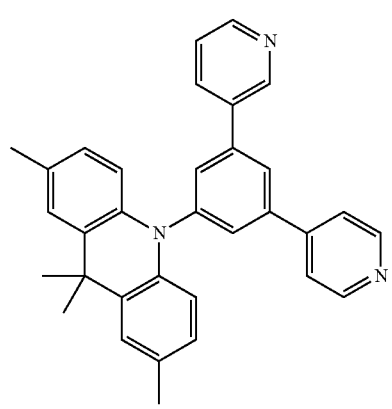

6
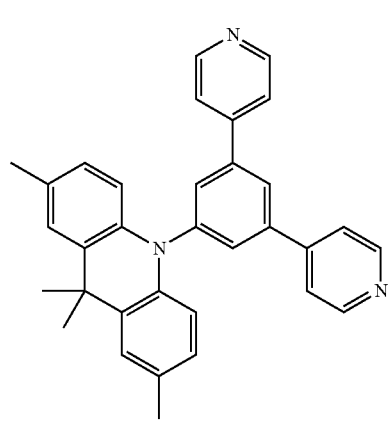

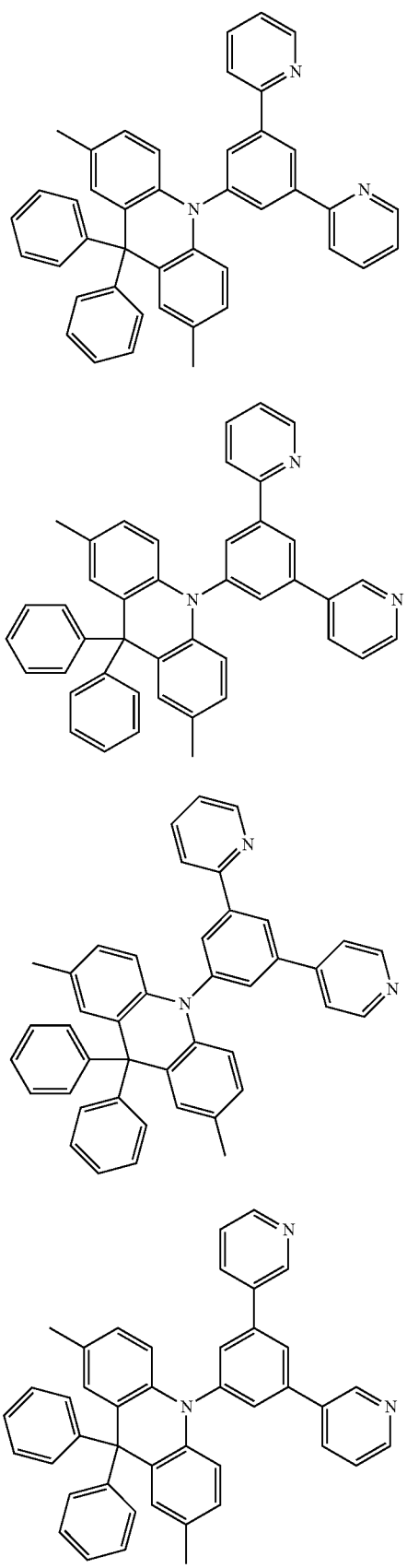
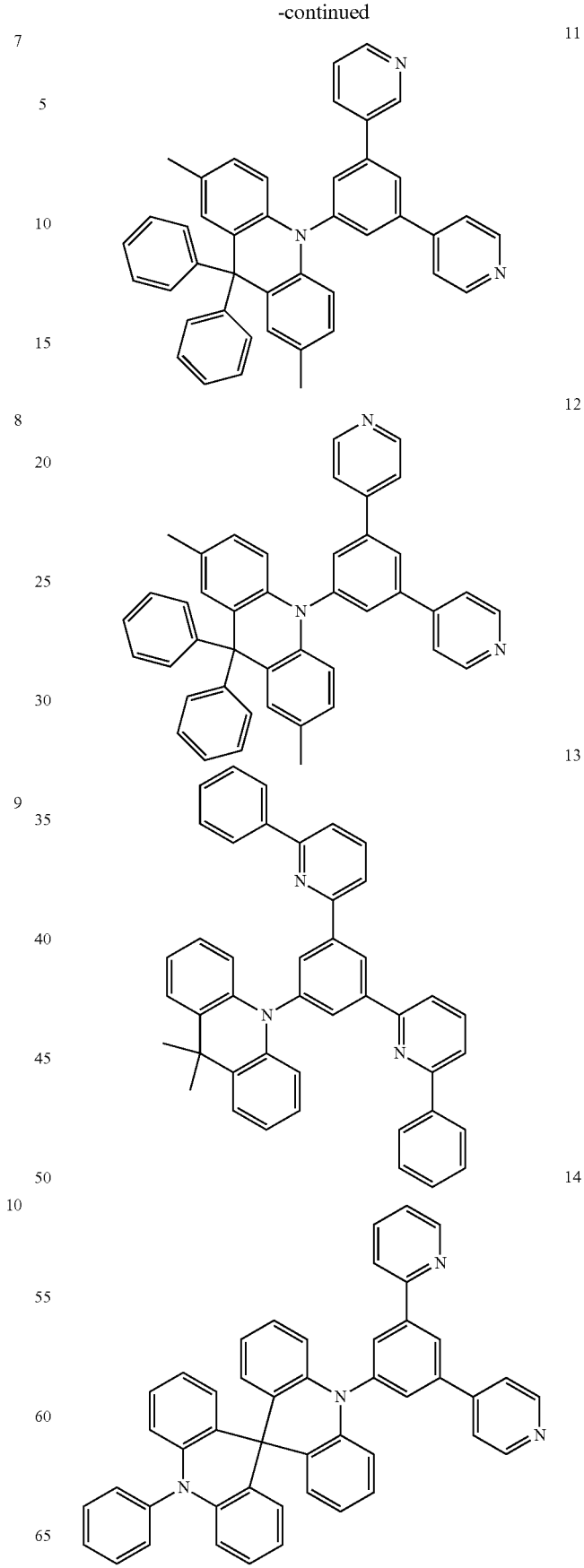

15
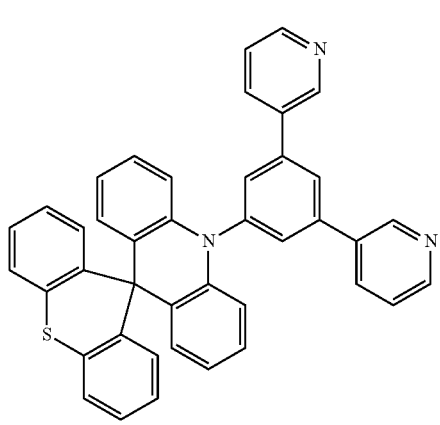
16
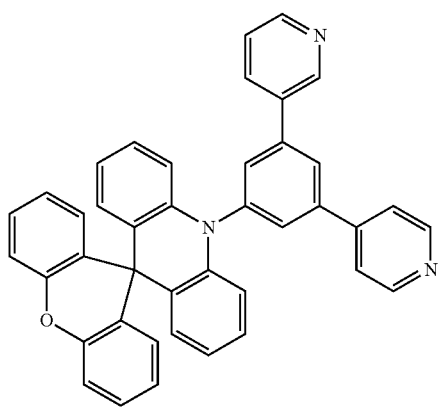
17
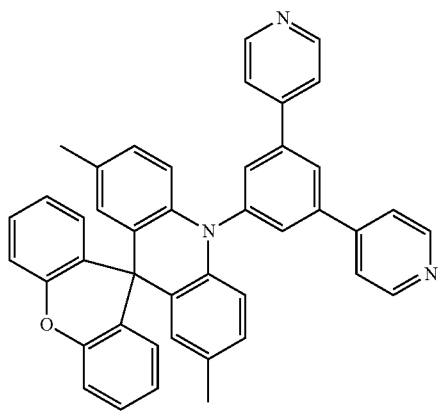
18
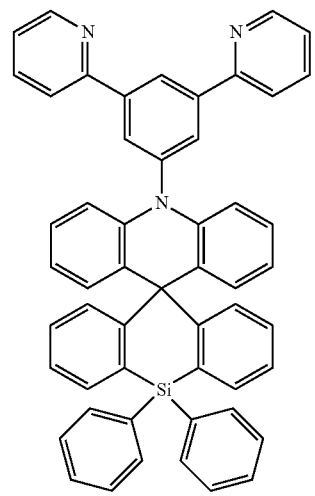
19
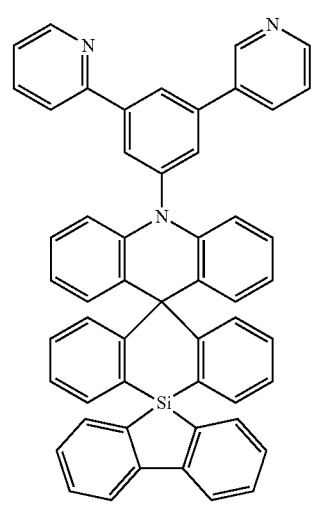
20
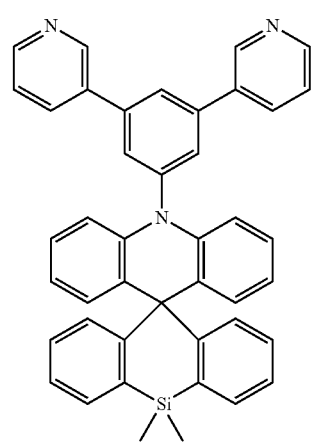

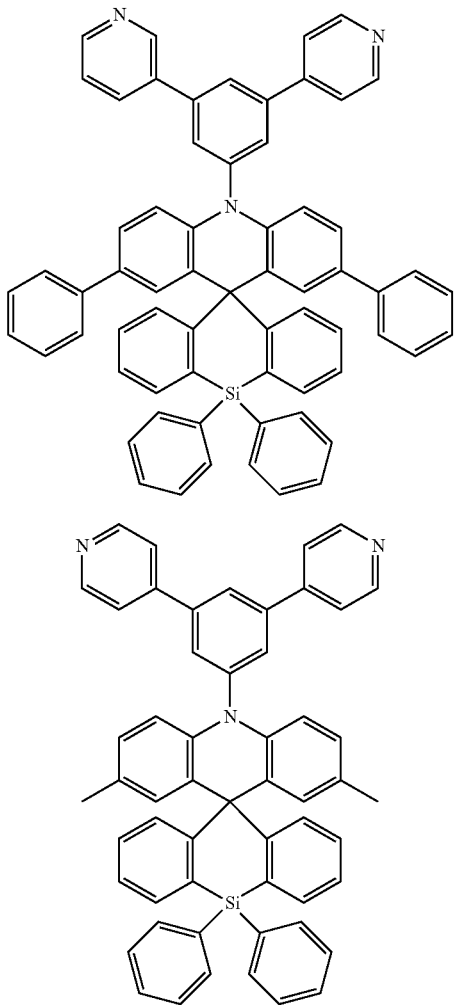

The nitrogen-containing compound of an embodiment may be used in an organic electroluminescence device and may help improve the efficiency and life of the organic electroluminescence device. The nitrogen-containing compound of an embodiment may be used as a material of an organic layer, which is disposed between opposite electrodes of an organic electroluminescence device. For example, the nitrogen-containing compound of an embodiment may be used as a material for an emission layer to help improve the emission efficiency of an organic electroluminescence device.

In addition, the nitrogen-containing compound of an embodiment may include both an electron donor and an electron acceptor in one compound unit, and Du (which is an electron donor) and a pyridine group (which is an electron acceptor) may be bonded to a meta position of a benzene ring which is a linker, to be used as a blue emission material which emits thermally activated delayed fluorescence by minimizing a difference between singlet energy and triplet energy and increasing a triplet energy level.

Hereinafter, an organic electroluminescence device according to an embodiment will be explained. Hereinafter, the above-described nitrogen-containing compound according to an embodiment may not be explained in particular, and unexplained parts will follow the above explanation on the nitrogen-containing compound according to an embodiment.

Figure 2:
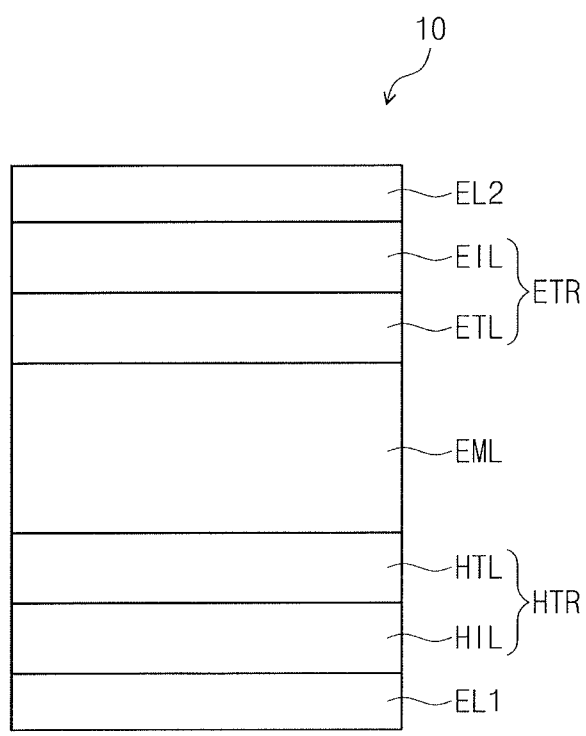

FIGS. 1 and 2 illustrate cross-sectional views of organic electroluminescence devices according to exemplary embodiments. Referring to FIGS. 1 and 2, an organic electroluminescence device 10 according to an embodiment may include a first electrode EL1, a hole transport region HTR, an emission layer EML, an electron transport region ETR, and a second electrode EL2 laminated one by one.

The first electrode EL1 and the second electrode EL2 are oppositely disposed from each other, and a plurality of organic layers may be disposed between the first electrode EL1 and the second electrode EL2. The plurality of the organic layers may include the hole transport region HTR, the emission layer EML, and the electron transport region ETR.

The organic electroluminescence device 10 of an embodiment may include the nitrogen-containing compound of an embodiment in at least one of a plurality of the organic layers disposed between the first electrode EL1 and the second electrode EL2. For example, the nitrogen-containing compound of an embodiment may be included in an emission layer EML.

Meanwhile, when compared with FIG. 1, FIG. 2 shows a cross-sectional view of an organic electroluminescence device of an embodiment, wherein a hole transport region HTR includes a hole injection layer HIL and a hole transport layer HTL, and an electron transport region ETR includes an electron injection layer EIL and an electron transport layer ETL.

The first electrode EL1 has conductivity. The first electrode EL1 may be formed using a metal alloy or a conductive compound. The first electrode EL1 may be an anode.

The first electrode EL1 may be a transmissive electrode, a transflective electrode, or a reflective electrode. In the case where the first electrode EL1 is the transmissive electrode, the first electrode EL1 may be formed using, e.g., a transparent metal oxide such as indium tin oxide (ITO), indium zinc oxide (IZO), zinc oxide (ZnO), and indium tin zinc oxide (ITZO). In the case where the first electrode EL1 is the transflective electrode or the reflective electrode, the first electrode EL1 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In an implementation, the first electrode EL1 may have a structure of a plurality of layers including a reflective layer, or a transflective layer formed using the above materials, and a transmissive conductive layer formed using ITO, IZO, ZnO, or ITZO. For example, the first electrode EL1 may include a plurality of layers of ITO/Ag/ITO.

The hole transport region HTR is provided on the first electrode EL1. The hole transport region HTR may include at least one of a hole injection layer HIL, a hole transport layer HTL, a hole buffer layer, or an electron blocking layer. The thickness of the hole transport region HTR may be, e.g., from about 1,000 Å to about 1,500 Å.

The hole transport region HTR may have a single layer formed using a single material, a single layer formed using a plurality of different materials, or a multilayer structure including a plurality of layers formed using a plurality of different materials.

In an implementation, the hole transport region HTR may have the structure of a single layer such as a hole injection layer HIL, or a hole transport layer HTL, and may have a structure of a single layer formed using a hole injection material and a hole transport material. In an implementation, the hole transport region HTR may have, e.g., a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL of the organic electroluminescence device 10 of an embodiment may include a suitable hole injection material. In an implementation, the hole injection layer HIL may include, e.g., triphenylamine-containing polyetherketone (TPAPEK), 4-isopropyl-4'-methyl-diphenyliodoniumtetrakis(pentafluorophenyl)borate (PPBL), N,N'-diphenyl-N,N'-bis-[4-(phenyl-m-tolyl-amino)-phenyl]-phenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), 4,4',4"-tris(N,N-diphenylamino)triphenylamine (TDATA), 4,4',4"-tris(N,N-2-naphthyphenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), or polyaniline/poly(4-styrenesulfonate) (PANI/PSS).

The hole transport layer HTL of the organic electroluminescence device 10 of an embodiment may include a suitable hole transport material. In an implementation, the hole transport layer HTL may include, e.g., 1,1-bis[(di-4-trileamino)phenyl]cyclohexane (TAPC), carbazole derivatives such as N-phenyl carbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphtyl)-N,N'-diphenylbenzidine (NPB), etc.

The thickness of the hole transport region HTR may be from about 100 Å to about 10,000 Å, e.g., from about 100 Å to about 1,000 Å. If the hole transport region HTR includes both the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, e.g., a p-dopant. The p-dopant may be one of quinone derivatives, metal oxides, or cyano group-containing compounds, without limitation. In an implementation, the p-dopant may include quinone derivatives such as tetracyanoquinodimethane (TCNQ) and 2,3,5,6-tetrafluoro-tetracyanoquinodimethane (F4-TCNQ), or metal oxides such as tungsten oxide, and molybdenum oxide.

As described above, the hole transport region HTR may further include at least one of a hole buffer layer or an electron blocking layer in addition to the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer.

In an implementation, the hole transport region HTR may further include an electron blocking layer, and the electron blocking layer may be disposed between the hole transport layer HTL and the emission layer EML. The electron blocking layer is a layer which plays the role of blocking electron injection from the electron transport region ETR to the hole transport region HTR. The electron blocking layer may use a suitable material for an electron blocking layer. In an implementation, the electron blocking layer may include, e.g., 1,3-bis(N-carbazolyl)benzene (mCP).

The emission layer EML is provided on the hole transport region HTR. In an implementation, the thickness of the emission layer EML may be, e.g., from about 100 Å to about 300 Å. In an implementation, the emission layer EML may have a single layer formed using a single material, a single layer formed using a plurality of different materials, or a multilayer structure having a plurality of layers formed using a plurality of different materials.

In an implementation, the emission layer EML may emit one of red, green, blue, white, yellow or cyan light. In an implementation, the emission layer EML may include a fluorescence emitting material or a phosphorescence emitting material.

In an implementation, the emission layer EML may include the nitrogen-containing compound of an embodiment. The organic electroluminescence device of an embodiment may include the nitrogen-containing compound, represented by Formula 1 to emit delayed fluorescence. In an implementation, the emission layer EML of the organic electroluminescence device 10 of an embodiment may be a layer including a nitrogen-containing compound, represented by Formula 1 and emitting blue light and thermally activated delayed fluorescence.

[Formula 1]

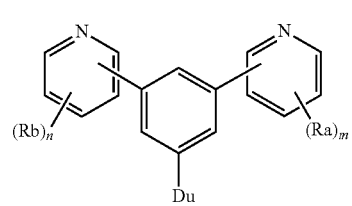

In Formula 1, Ra and Rb may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In Formula 1, m and n may each independently be, e.g., an integer of 0 to 4.

In Formula 1, Du may be, e.g., a group represented by the following Formula 2-1 or Formula 2-2.

[Formula 2-1]

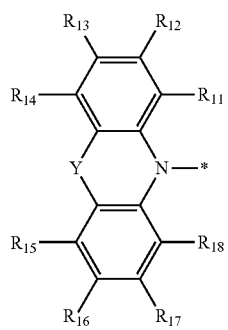

[Formula 2-2]

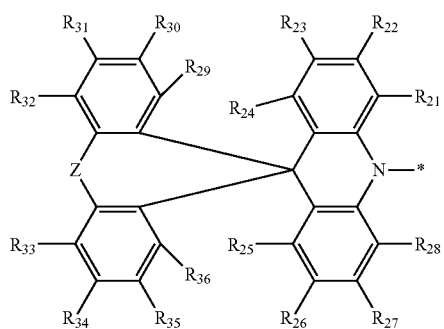

In Formulae 2-1 and 2-2, Y may be, e.g., $CR_1R_2$, or $NR_3$, and Z may be, e.g., O, S, $CR_4R_5$, $NR_6$, or $SiR_7R_8$. $R_1$ to $R_8$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_1$ and $R_2$, $R_4$ and $R_5$, and $R_7$ and $R_8$, may be each independently combined with each other to form a ring.

$R_{11}$ to $R_{18}$, and $R_{21}$ to $R_{36}$ may each independently be or include, e.g., a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In $R_{11}$ to $R_{18}$, and $R_{21}$ to $R_{36}$, substituents of the substituted or unsubstituted alkyl group having 1 to 10 carbon atoms, the substituted or unsubstituted aryl group having 6 to 30 ring carbon atoms, and the substituted or unsubstituted heteroaryl group having 2 to 30 ring carbon atoms may each independently be, e.g., a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms.

In addition, for explaining the compound containing nitrogen, represented by Formula 1 which is used in the emission layer EML of the organic electroluminescence device of an embodiment, the same explanation on the nitrogen-containing compound of an embodiment may be applied to that of Du, Ra, Rb, m, n, Y, Z, $R_{11}$ to $R_{18}$, and $R_{21}$ to $R_{36}$.

In an implementation, the emission layer EML in the organic electroluminescence device of an embodiment may include the nitrogen-containing compound, represented by the following Formula 1-1 to Formula 1-3.

[Formula 1-1]

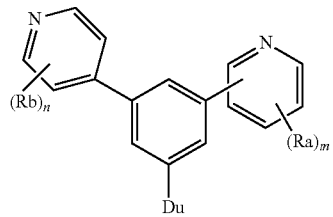

[Formula 1-2]

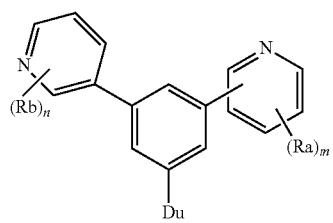

[Formula 1-3]

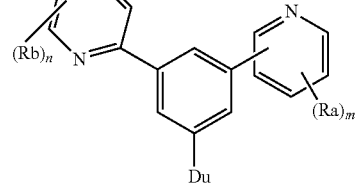

In Formula 1-1 to Formula 1-3, the same explanation on the nitrogen-containing compound of an embodiment may be applied to that of Du, Ra, Rb, m and n.

The emission layer EML of the organic electroluminescence device of an embodiment may include a nitrogen-containing compound, represented by Formula 1, and Du in Formula 1 may be, e.g., a group represented by one of the following Formula 2a to Formula 2i.

[Formula 2a]

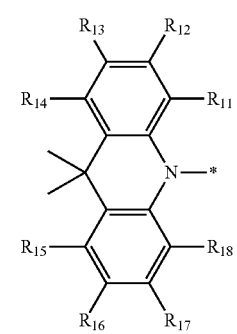

-continued

[Formula 2b]

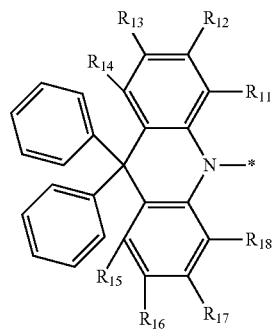

[Formula 2c]

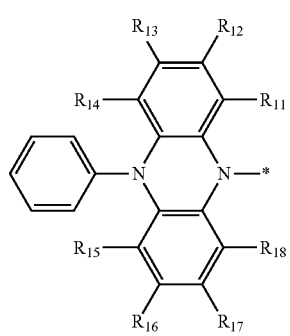

[Formula 2d]

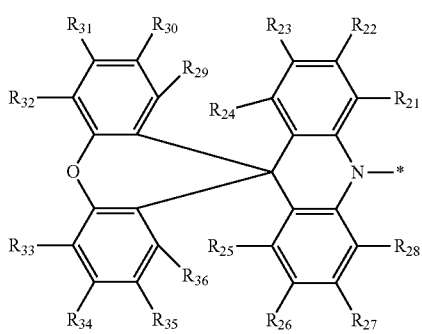

[Formula 2e]

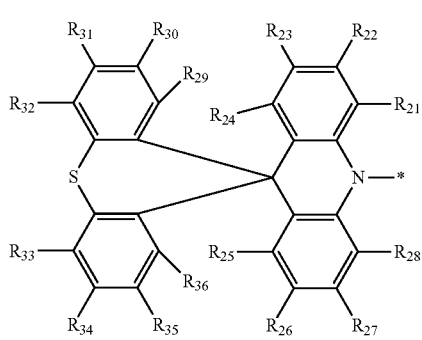

[Formula 2f]

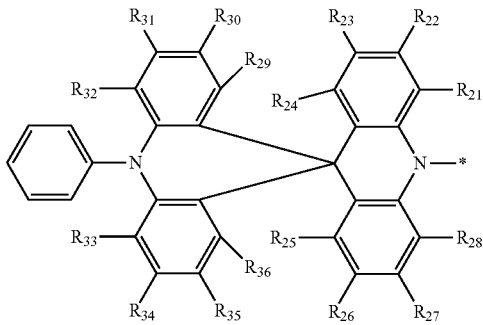

[Formula 2g]

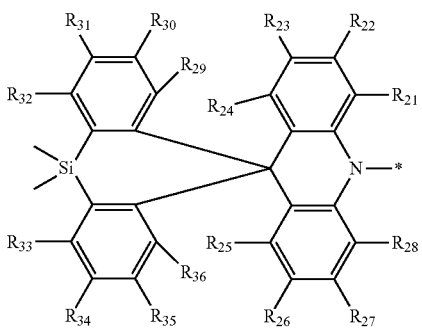

[Formula 2h]

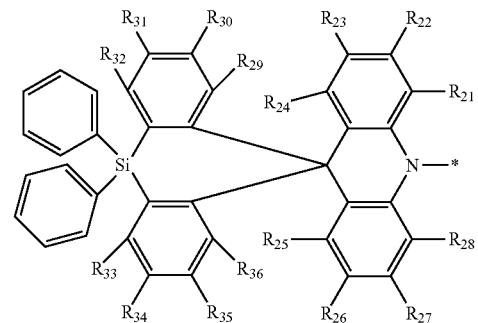

[Formula 2i]

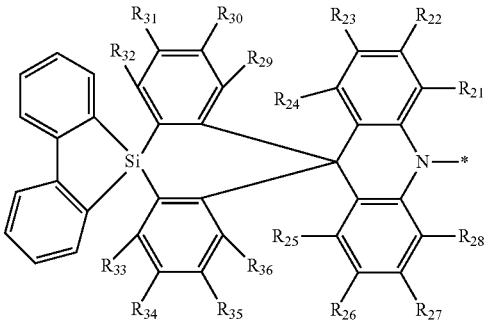

In Formula 2a to Formula 2i, the same explanation on $R_{11}$ to $R_{18}$, and $R_{21}$ to $R_{36}$ of Formula 2 may be applied to that $R_{11}$ to $R_{18}$, and $R_{21}$ to $R_{36}$.

In the organic electroluminescence device 10 of an embodiment, the emission layer EML may include a host and a dopant. In this case, the emission layer EML may have a thickness of about 100 Å to about 600 Å. In an implementation, the emission layer EML may be a phosphorescence emission layer or a fluorescence emission layer.

For example, the emission layer EML may be a fluorescence emission layer in an embodiment. The emission layer EML of an organic electroluminescence device 10 of an embodiment may be a delayed fluorescence emission layer. For example, a portion of the light emitted from the emission layer EML may be due to thermally activated delayed fluorescence.

If the organic electroluminescence device 10 of an embodiment includes an emission layer EML which emits delayed fluorescence, the emission layer EML may include the nitrogen-containing compound of an embodiment. In an implementation, the nitrogen-containing compound of an embodiment may be a delayed fluorescence material, e.g., the nitrogen-containing compound of an embodiment may be a material for thermally activated delayed fluorescence.

The nitrogen-containing compound of an embodiment may be a material for delayed fluorescence, which emits blue light. For example, the nitrogen-containing compound of an embodiment may be a material for thermally activated delayed fluorescence, which emits blue light.

The emission layer EML of the organic electroluminescence device 10 of an embodiment, including the nitrogen-containing compound of an embodiment may emit blue light. In an implementation, the nitrogen-containing compound of an embodiment may be a material for thermally activated delayed fluorescence, which emits green light or blue light.

In an implementation, the emission layer EML emitting delayed fluorescence may include a host and a dopant, and the host may be a host for emitting delayed fluorescence, and the dopant may be a dopant for emitting delayed fluorescence.

The nitrogen-containing compound according to an embodiment may be included as a dopant material of an emission layer EML. In an implementation, the nitrogen-containing compound of an embodiment may be used as a dopant material which emits delayed fluorescence. In an implementation, the emission layer EML may be a delayed fluorescence emission layer, and the emission layer EML may include a suitable host material and the nitrogen-containing compound of an embodiment. For example, the nitrogen-containing compound according to an embodiment may be used as a TADF dopant.

In an implementation, the emission layer EML may include a suitable host material. In an implementation, the emission layer EML may include as a host material, e.g., tris(8-hydroxyquinolino)aluminum (Alq3), 4,4'-bis(N-carbazolyl)-1,1'-biphenyl (CBP), poly(N-vinylcarbazole) (PVK), 9,10-di(naphthalene-2-yl)anthracene (ADN), 4,4', 4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CPI), 1,4-bis (triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), 3,3'-bis(N-carbazolyl)-1,1'-biphenyl (mCBP), 1,3-bis(N-carbazolyl) benzene (mCP), etc. In an implementation, a host material emitting delayed fluorescence may be included in addition to the suggested host material.

In an implementation, the emission layer EML may further include a suitable dopant material in the organic electroluminescence device 10 of an embodiment. In an implementation, the emission layer EML may include, as a dopant, e.g. styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

The electron transport region ETR may be provided on the emission layer EML. In an implementation, the electron transport region ETR may include at least one of an electron blocking layer, an electron transport layer ETL or an electron injection layer EIL.

In an implementation, the electron transport region ETR may have a single layer formed using a single material, a single layer formed using a plurality of different materials, or a multilayer structure having a plurality of layers formed using a plurality of different materials.

In an implementation, the electron transport region ETR may have a single layer structure of the electron injection layer EIL or the electron transport layer ETL, or a single layer structure formed using an electron injection material and an electron transport material. In an implementation, the electron transport region ETR may have a single layer structure having a plurality of different materials, or a structure laminated from the first electrode EL1 of electron transport layer ETL/electron injection layer EIL, or hole blocking layer/electron transport layer ETL/electron injection layer EIL. The thickness of the electron transport region ETR may be, e.g., from about 100 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In an implementation, the electron transport region ETR may include an electron transport layer ETL, and the electron transport region ETR may include, e.g., tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d] imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalene-2-yl)anthracene (ADN), or a mixture thereof.

If the electron transport region ETR includes the electron transport layer ETL, the thickness of the electron transport layer ETL may be from about 100 Å to about 1,000 Å, e.g., from about 150 Å to about 500 Å. If the thickness of the electron transport layer ETL satisfies the above-described range, satisfactory electron transport properties may be obtained without substantial increase of a driving voltage.

In an implementation, the electron transport region ETR may include the electron injection layer EIL, and the electron transport region ETR may include, e.g., LiF, lithium quinolate (LiQ), $Li_2O$, BaO, NaCl, CsF, a metal in lanthanoides such as Yb, or a metal halide such as RbCl, RbI and KI. In an implementation, the electron injection layer EIL may be formed using a mixture material of an electron transport material and an insulating organo metal salt. The organo metal salt may be a material having an energy band gap of about 4 eV or more. In an implementation, the organo metal salt may include, for example, metal acetates, metal benzoates, metal acetoacetates, metal acetylacetonates, or metal stearates.

If the electron transport region ETR includes the electron injection layer EIL, the thickness of the electron injection layer EIL may be from about 1 Å to about 100 Å, e.g., from about 3 Å to about 90 Å. If the thickness of the electron injection layer EIL satisfies the above described range, satisfactory electron injection properties may be obtained without inducing the substantial increase of a driving voltage.

The electron transport region ETR may include a hole blocking layer as described above. In an implementation, the hole blocking layer may include at least one of, e.g., 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 has conductivity. The second electrode EL2 may be formed using a metal alloy or a conductive compound. The second electrode EL2 may be a cathode. The second electrode EL2 may be a transmissive electrode, a transflective electrode or a reflective electrode. If the second electrode EL2 is the transmissive electrode, the second electrode EL2 may include a transparent metal oxide, e.g., ITO, IZO, ZnO, ITZO, etc.

If the second electrode EL2 is the transflective electrode or the reflective electrode, the second electrode EL2 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In an implementation, the second electrode EL2 may have a multilayered structure including a reflective layer or a transflective layer formed using the above-described materials and a transparent conductive layer formed using ITO, IZO, ZnO, ITZO, etc.

In an implementation, the second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

If the organic electroluminescence device 10 is a top emission type, the first electrode EL1 may be a reflective electrode and the second electrode EL2 may be a transmissive electrode or a transflective electrode. If the organic electroluminescence device 10 is a bottom emission type, the first electrode EL1 may be a transmissive electrode or a transflective electrode and the second electrode EL2 may be a reflective electrode.

The organic electroluminescence device 10 of an embodiment may include at least one compound represented in Compound Group 1 below in an emission layer EML.

In an implementation, the organic electroluminescence device 10 of an embodiment may use at least one of the compounds of Compound Group 1, below, as a dopant material of an emission layer EML. In an implementation, the organic electroluminescence device 10 of an embodiment may include at least one of the compounds of Compound Group 1, below, as a material for emitting thermally activated delayed fluorescence.

[Compound Group 1]

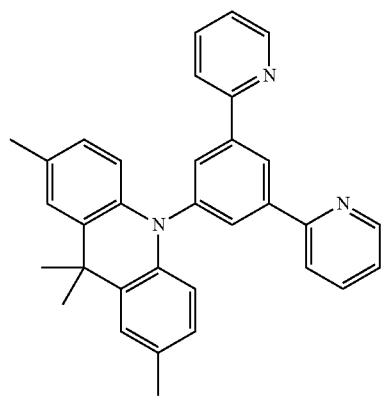

1

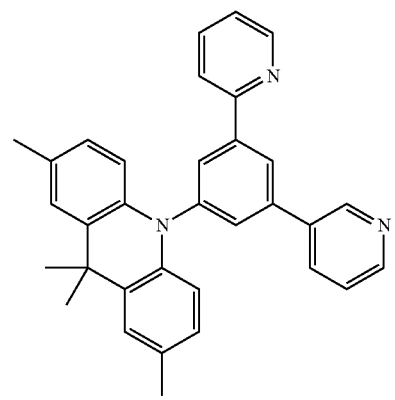

2

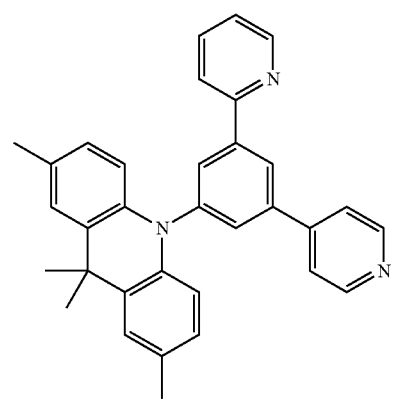

3

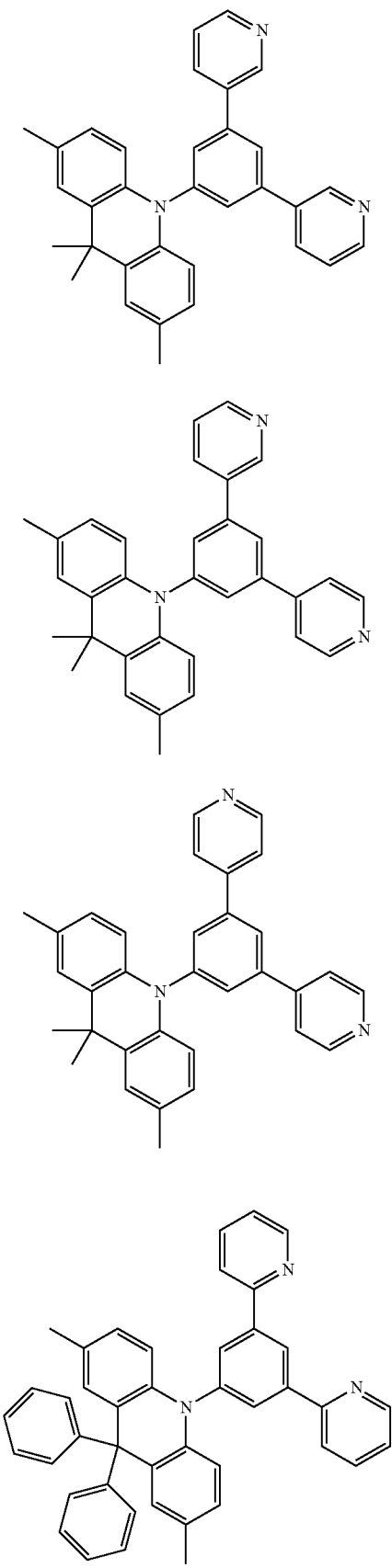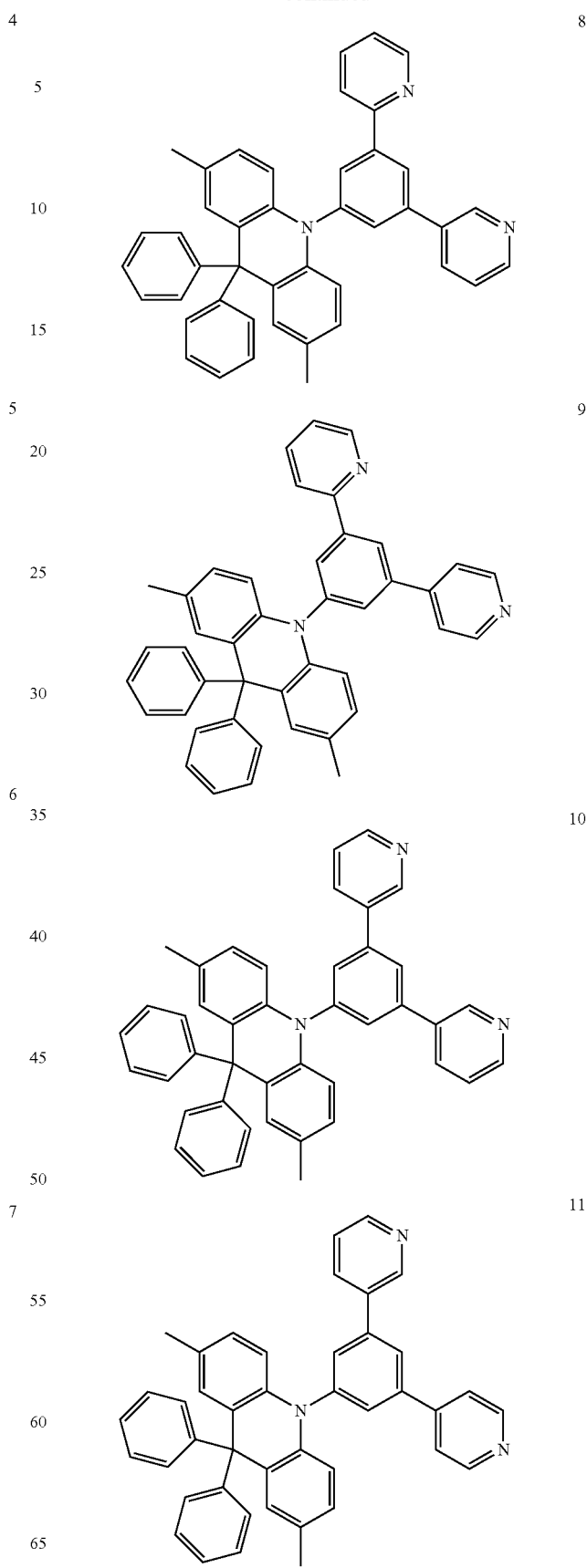

12
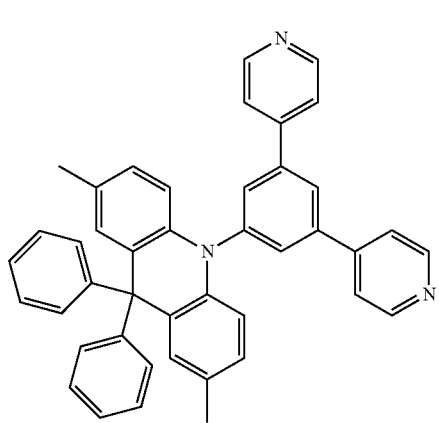
13
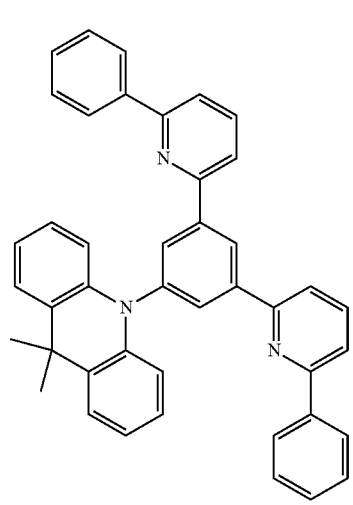
14
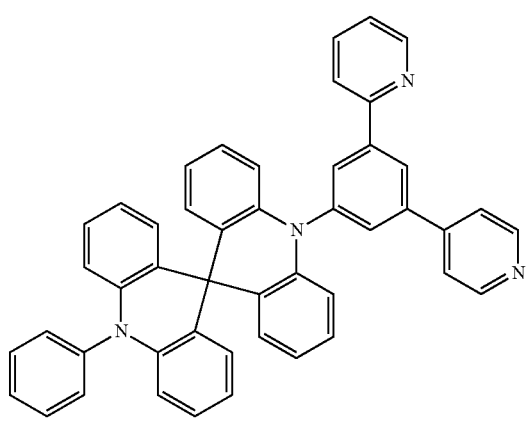
15
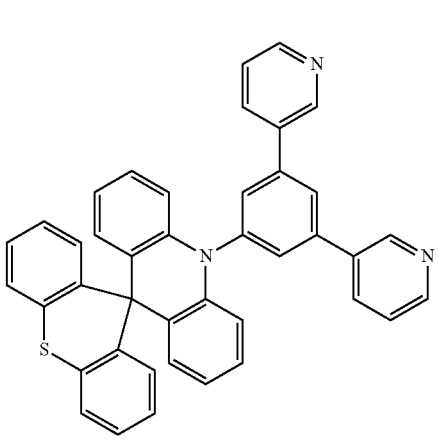
16
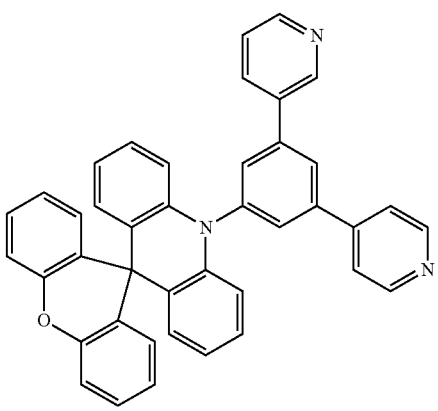
17
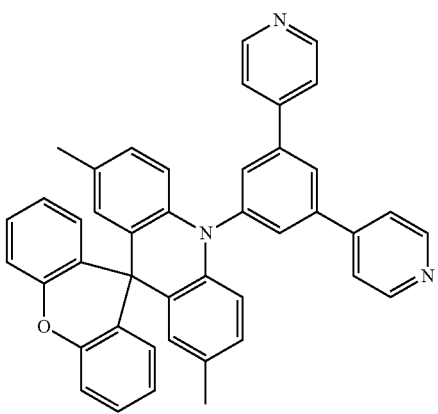

18

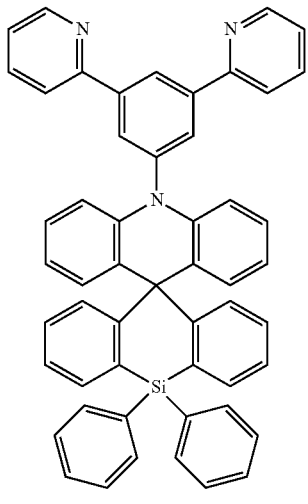

19

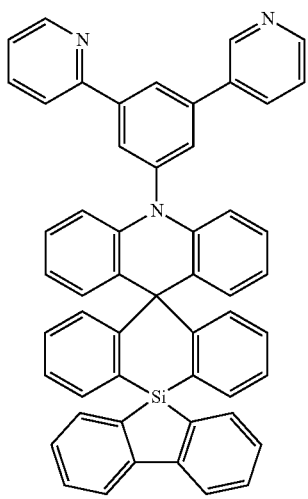

20

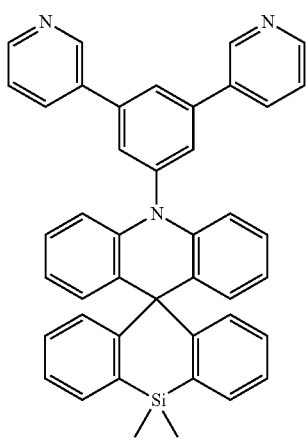

21

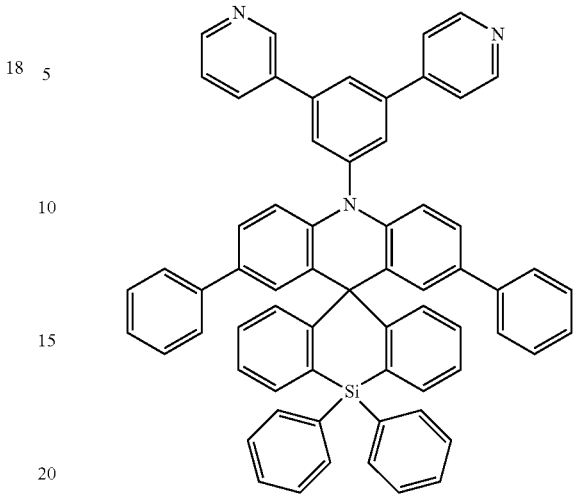

22

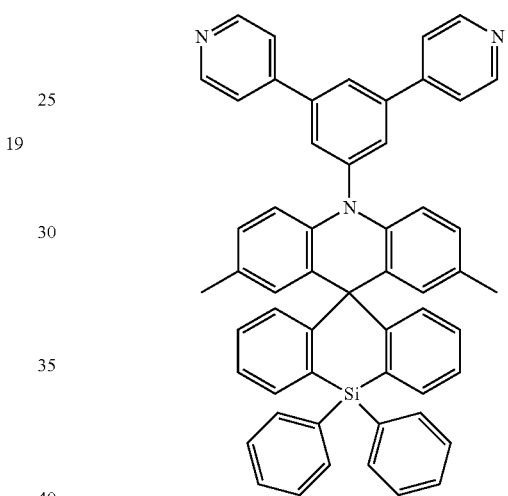

The organic electroluminescence device of an embodiment may include the nitrogen-containing compound of an embodiment and may have improved emission efficiency and life. In addition, the organic electroluminescence device of an embodiment includes the nitrogen-containing compound in an emission layer and may help improve emission efficiency. In addition, the organic electroluminescence device of an embodiment may use the nitrogen-containing compound of an embodiment as a material for emitting delayed fluorescence, and emission efficiency in a blue light region may be even further improved.

Hereinafter a nitrogen-containing compound according to an embodiment and an organic electroluminescence device including the nitrogen-containing compound according to an embodiment will be explained in more detail with reference to embodiments and comparative embodiments. The following embodiments are only illustrations to assist in understanding.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Examples

1. Synthesis of Nitrogen-Containing Compound

First, the synthetic method of the nitrogen-containing compound according to an embodiment will be particularly explained referring to the synthetic methods of Compound 6, Compound 10, Compound 12, and Compound 13.

(Synthesis of Compound 6)

Compound 6 including nitrogen according to an embodiment was synthesized according to Reaction Scheme 1 below.

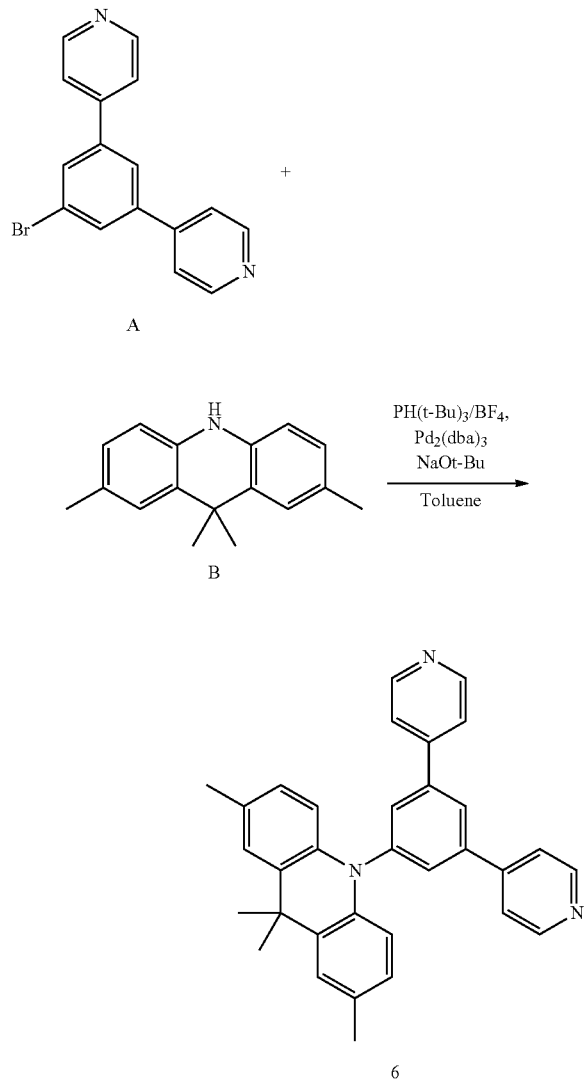

Under an argon atmosphere, to a 100 ml, three neck flask, 1.5 g of Compound A, 1.1 g of Compound B, 0.88 g of tris(dibenzylideneacetone)dipalladium ($Pd_2(dba)_3$), 0.11 g of $PH(tBu)_3/BF_4$, and 0.93 g of sodium t-butoxide (NaOt-Bu) were added, followed by heating and refluxing in a toluene solvent for about 15 hours. After cooling in the air, water was added, an organic layer was separated, and solvents were removed by distillation. The crude product thus obtained was separated by silica gel chromatography (using a mixed solvent of ethyl acetate and methylene chloride), and recrystallized using hexane to obtain 1.12 g (yield 53%) of a target product as a white solid.

The molecular weight of the target product measured by FAB-MS was 440. From the results, the target product was identified as Compound 6.

(Synthesis of Compound 10)

Compound 10 including nitrogen according to an embodiment was synthesized according to Reaction Scheme 2 below.

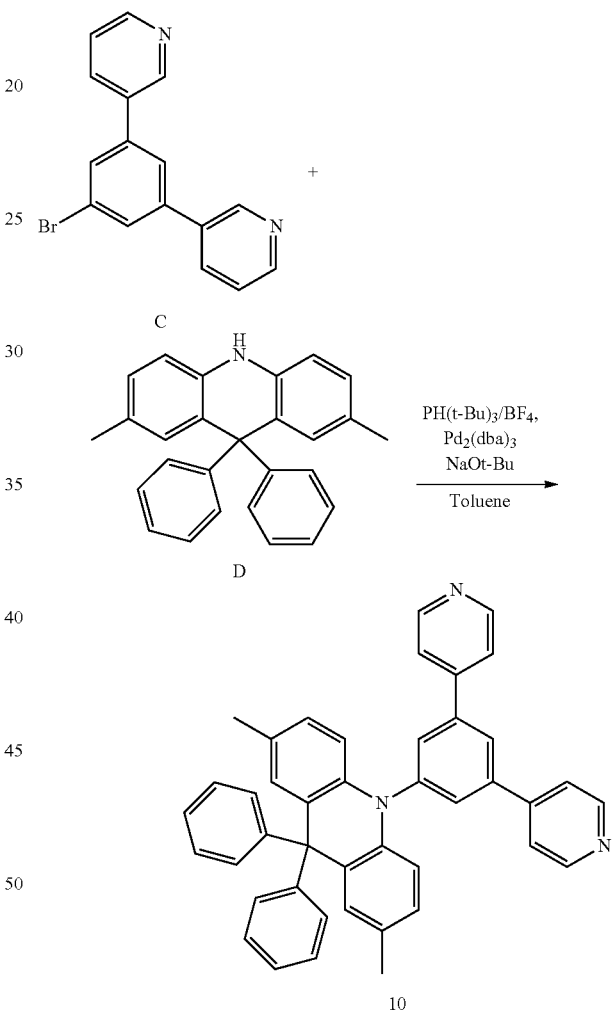

The same method as the synthetic method of Compound 6 was conducted except for using Compound C instead of Compound A and using Compound D instead of Compound B in the synthetic method to obtain Compound 10 (yield 68%) as a target product. The molecular weight of the target product measured by FAB-MS was 592.

(Synthesis of Compound 12)

Compound 12 including nitrogen according to an embodiment was synthesized according to Reaction Scheme 3 below.

[Reaction Scheme 3]

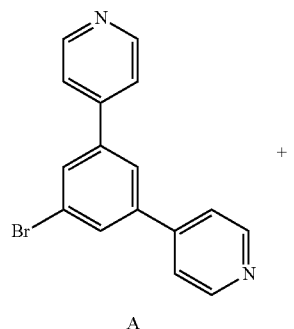

A

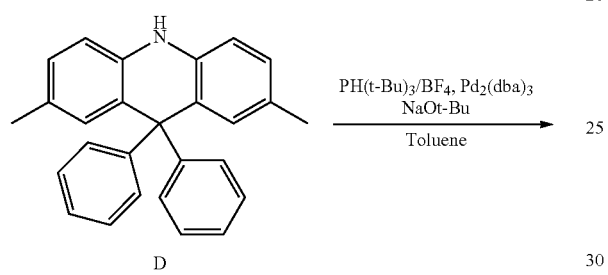

D

[Reaction Scheme 4]

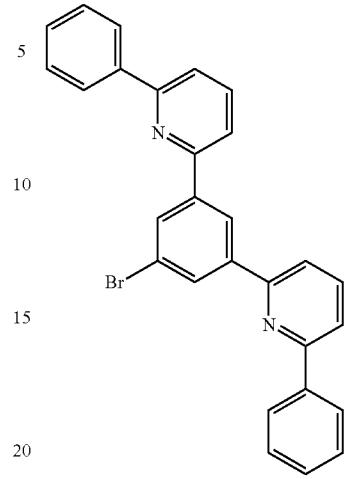

E

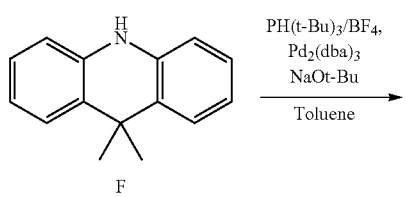

F

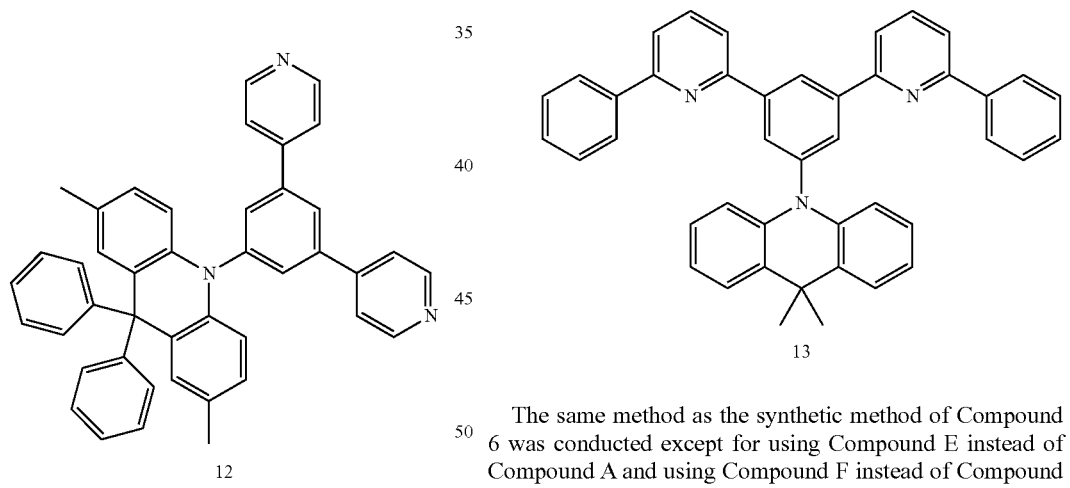

12

13

The same method as the synthetic method of Compound 6 was conducted except for using Compound D instead of Compound B in the synthetic method to obtain Compound 12 (yield 73%) as a target product. The molecular weight of the target product measured by FAB-MS was 592.

(Synthesis of Compound 13)

Compound 13 including nitrogen according to an embodiment was synthesized according to Reaction Scheme 4 below.

The same method as the synthetic method of Compound 6 was conducted except for using Compound E instead of Compound A and using Compound F instead of Compound B in the synthetic method to obtain Compound 13 (yield 85%) as a target product. The molecular weight of the target product measured by FAB-MS was 592.

2. Manufacture and Evaluation of Organic Electroluminescence Device Including a Nitrogen-Containing Compound (Manufacture of Organic Electroluminescence Device)

An organic electroluminescence device of was manufactured by the method below. Organic electroluminescence devices of Examples 1 to 4 were manufactured using the nitrogen-containing compound of Compound 6, Compound 10, Compound 12, and Compound 13 as materials for an emission layer. In Table 1, the compounds used in Example 1 to Example 4 and Comparative Example 1 to Comparative Example 4 are listed.

TABLE 1
Compound 6
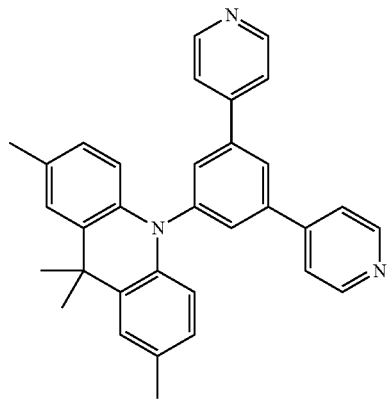
6
Comparative
Compound X-1
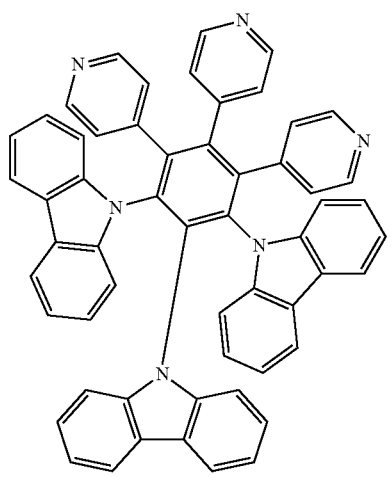 [SMILES: c1ccc2c(c1)c1ccccc1n2-c1c(-c2ccncc2)c(-c2ccncc2)c(-c2ccncc2)c(-n2c3ccccc3c3ccccc32)c1-n1c2ccccc2c2ccccc21]
Compound 10
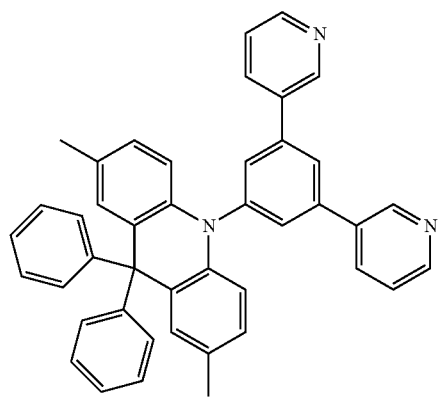
10

TABLE 1-continued
Comparative Compound X-2
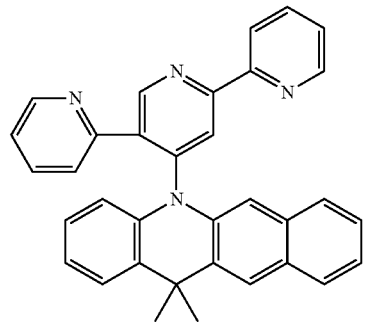 [SMILES: CC1(C)c2ccccc2N(c2cc(-c3ccccn3)ncc2-c2ccccn2)c2cc3ccccc3cc21]
Compound 12
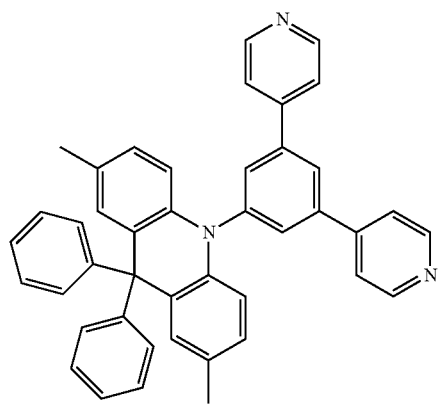
12
Comparative Compound X-3
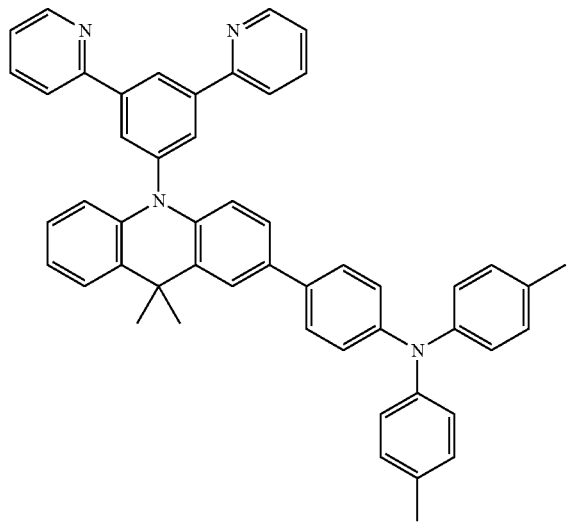 [SMILES: Cc1ccc(N(c2ccc(C)cc2)c2ccc(-c3ccc4c(c3)C(C)(C)c3ccccc3N4c3cc(-c4ccccn4)cc(-c4ccccn4)c3)cc2)cc1]

TABLE 1-continued

Compound 13

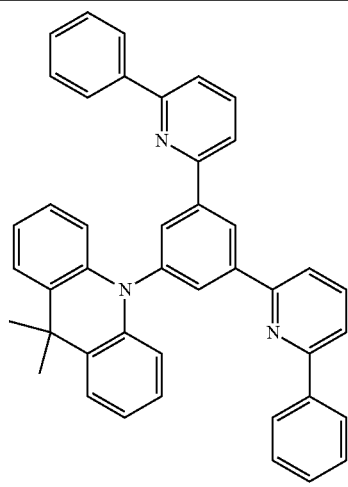

13

Comparative
Compound X-4

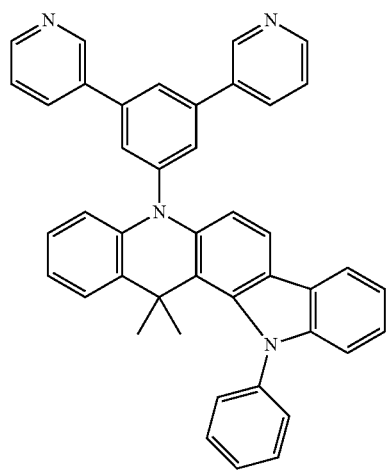 [SMILES: CC1(C)c2ccccc2N(c2cc(-c3cccnc3)cc(-c3cccnc3)c2)c2ccc3c4ccccc4n(-c4ccccc4)c3c21]

The organic electroluminescence devices of the Examples and the Comparative Examples were manufactured by the method described below.

On a glass substrate, ITO was patterned to a thickness of about 1,500 Å and washed with ultra-pure water, and a UV ozone treatment was conducted for about 10 minutes. Then, HAT-CN was deposited to a thickness of about 100 Å, α-NPD was deposited to a thickness of about 800 Å, and mCP was deposited to a thickness of about 50 Å to form a hole transport region.

Then, the nitrogen-containing compound or the Comparative Compound was co-deposited with DPEPO in a weight ratio of 18:82 during forming an emission layer to form a layer to a thickness of about 200 Å. After that, another layer was formed using DPEPO to a thickness of about 100 Å. For example, the emission layer formed by the co-deposition was obtained by depositing a mixture of each of Compounds 6, 10, 12 and 13 with DPEPO in Example 1 to Example 4 and by depositing a mixture of each of Comparative Compounds X-1, X-2, X-3, and X-4 with DPEPO in Comparative Example 1 to Comparative Example 4.

On the emission layer, a layer was formed using TPBi to a thickness of about 300 Å, and a layer was formed using LiF to a thickness of about 5 Å to form an electron transport region. Then, a second electrode was formed using aluminum (Al) to a thickness of about 1,000 Å.

In an implementation, a hole transport region, an emission layer, an electron transport region and a second electrode were formed by using a vacuum deposition apparatus.

(Energy Level of Compounds)

In Table 2 below, the singlet energy level (S1 energy level) and the triplet energy level (T1 energy level) of Example Compounds 6, 10, 12, and 13 and Comparative Compounds X-1, X-2, X-3, and X-4 are shown. In Table 2, energy level values were calculated by a non-empirical molecular orbital method, viz., calculated by B3LYP/6-31G (d) using Gaussian 09 of Gaussian Co., Ltd. $E_{ST}$ means the difference between the singlet energy level (S1 energy level) and the triplet energy level (T1 energy level).

TABLE 2

| Compound | S1 energy level | T1 energy level | $E_{ST}$ |
|---|---|---|---|
| Compound 6 | 2.91 | 2.87 | 0.04 |
| Compound 10 | 3.00 | 2.97 | 0.03 |
| Compound 12 | 2.85 | 2.82 | 0.03 |
| Compound 13 | 2.74 | 2.70 | 0.04 |

TABLE 2-continued

| Compound | S1 energy level | T1 energy level | $E_{ST}$ |
|---|---|---|---|
| Comparative Compound X-1 | 3.14 | 2.98 | 0.16 |
| Comparative Compound X-2 | 2.59 | 2.52 | 0.07 |
| Comparative Compound X-3 | 2.59 | 2.56 | 0.03 |
| Comparative Compound X-4 | 2.87 | 2.76 | 0.12 |

All Example Compounds 6, 10, 12, and 13 showed about 0.1 eV or less of low $E_{ST}$ values, and at the same time, about 2.70 eV or more of high triplet energy levels. In comparison, Comparative Compounds X-1 and X-4 showed about 2.70 eV or more of high triplet energy levels but $E_{ST}$ of greater than about 0.1 eV, and Comparative Compounds X-2 and X-3 showed $E_{ST}$ of about 0.1 eV or less but lower triplet energy levels than those of the example compounds.

For example, the example compounds had small $E_{ST}$ and at the same time high triplet energy levels, and may be used as a material for thermally activated delayed fluorescence with high efficiency. For example, due to the high triplet energy level, the example compounds may achieve thermally activated delayed fluorescence emission with deep blue color.

The example compounds may show high emission efficiency in a blue emission region when compared to the comparative compounds.

(Evaluation of Properties of Organic Electroluminescence Device)

In order to evaluate the properties of the organic electroluminescence devices according to the Examples and the Comparative Examples, the maximum emission wavelength ($\lambda_{max}$) and external quantum efficiency ($\eta_{ext}$) were measured. The maximum emission wavelength ($\lambda_{man}$) means a wavelength at a position where the maximum emission luminance is obtained at an emission peak. The evaluation of the properties of the organic electroluminescence device was conducted at ambient temperature, and the external quantum efficiency of the organic electroluminescence device was measured by using of an external quantum efficiency measurement apparatus, C9920-12 of HAMAMATSU Photonics Co., Ltd.

TABLE 3

| Category | Emission layer dopant | $\lambda_{max}$ (nm) | $\eta_{ext}$ (%) |
|---|---|---|---|
| Example 1 | Compound 6 | 469 | 7.6 |
| Example 2 | Compound 10 | 447 | 6.5 |
| Example 3 | Compound 12 | 474 | 8.3 |
| Example 4 | Compound 13 | 495 | 10.3 |
| Comparative Example 1 | Comparative Compound X-1 | 493 | 4.8 |
| Comparative Example 2 | Comparative Compound X-2 | 520 | 5.2 |
| Comparative Example 3 | Comparative Compound X-3 | 518 | 5.9 |
| Comparative Example 4 | Comparative Compound X-4 | 495 | 3.8 |

Referring to Table 3, the organic electroluminescence devices of Example 1 to Example 4, which included the compounds including nitrogen of exemplary embodiments as dopant materials of an emission layer showed higher external quantum efficiency when compared to Comparative Example 1 to Comparative Example 4. In addition, the organic electroluminescence devices of Example 1 to Example 4, which included the compounds including nitrogen of exemplary embodiments as dopant materials of an emission layer were found to have the maximum emission wavelength of about 495 nm or less and emit blue light. Example 1 to Example 4 were found to show higher external quantum efficiency than Comparative Example 2 and Comparative Example 3 and show the maximum emission wavelength in a shorter wavelength.

In addition, the maximum emission wavelength of Comparative Example 1 and Comparative Example 4 was similar to the emission wavelength region of Example 1 to Example 4, but had a relatively lower value of the external quantum efficiency than the examples.

For example, the organic electroluminescence device of an embodiment may include the nitrogen-containing compound in an emission layer and may achieve deep blue color which has a relatively short wavelength and at the same time, may show high emission efficiency.

In an implementation, a Du part (which is an electron donor) and pyridine groups which are electron acceptors are bonded to meta positions of a benzene ring which is a linker, so that a nitrogen-containing compound shows a low $E_{ST}$ value and a high triplet energy level.

When compared to the Examples, Comparative Compound X-1 included a carbazole group as an electron donor and shows a higher $E_{ST}$ value when compared to the Example compounds, and thus, the organic electroluminescence device of Comparative Example 1 showed lower external quantum efficiency when compared to the Examples.

Comparative Compound X-2 of Comparative Example 2 had a structure in which a n conjugated system of an acridine group was expanded and three pyridine groups were bonded, and showed a lower T1 energy level when compared to the example compounds, thereby showing the maximum emission wavelength with a longer wavelength and lower external quantum efficiency when compared to those of the Examples.

In Comparative Compound X-3 of Comparative Example 3, an acridine group was substituted with arylamine and a π conjugated system was expanded, thereby showing the maximum emission wavelength with a longer wavelength and lower external quantum efficiency when compared to those of the Examples.

In addition, in Comparative Compound X-4 of Comparative Example 4, cyclocondensation of an indole group with an acridine group was conducted and a π conjugated system was expanded, an $E_{ST}$ value was increased, the ratio of delayed fluorescence was decreased, and external quantum efficiency was found low.

Referring to Table 3, the organic electroluminescence device of the Examples, using a nitrogen-containing compound of an embodiment as an emission material of an emission layer, exhibited higher emission efficiency when compared to the Comparative Examples. In addition, with respect to an emission wavelength, the maximum emission wavelength of about 495 nm or less was shown and deep blue color was achieved.

By way of summation and review, in order to accomplish an organic electroluminescence device having high efficiency, a technique on phosphorescence emission using energy in a triplet state or a delayed fluorescence emission using a phenomenon of producing singlet excitons by the collision of triplet excitons (triplet-triplet annihilation, TTA) may be considered, and a thermally activated delayed fluorescence (TADF) material using delayed fluorescence phenomenon may be considered.

The organic electroluminescence device of an embodiment may achieve high emission efficiency in a blue color wavelength region by using a nitrogen-containing compound of an embodiment, in which the bonding positions of an electron donor and an electron acceptor are appropriately controlled, as a material of an emission layer.

In addition, a nitrogen-containing compound of an embodiment may include an electron donor and an electron acceptor in a molecule, and may have a high triplet energy value and at the same time maintains an absolute value of a difference between a singlet energy level and a triplet energy level low, thereby being used as a material for emitting delayed fluorescence. If the nitrogen-containing compound of an embodiment is used as a material for emitting delayed fluorescence, the emission efficiency of an organic electroluminescence device of an embodiment may be further improved.

The nitrogen-containing compound according to an embodiment may help improve the life and efficiency of an organic electroluminescence device.

The organic electroluminescence device according to an embodiment may include the nitrogen-containing compound of an embodiment in an emission layer, and may achieve high efficiency and long life.

The embodiments may provide a nitrogen-containing compound for an organic electroluminescence device having long life and high efficiency.

The embodiments may provide a nitrogen-containing compound, used as a thermally activated delayed fluorescence material and an organic electroluminescence device including the same in an emission layer.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A nitrogen-containing compound represented by the following Formula 1:

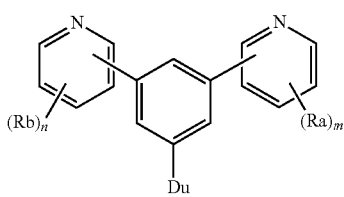

[Formula 1]

wherein, in Formula 1,

Ra and Rb are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, m and n are each independently an integer of 0 to 4, and Du is a group represented by the following Formula 2-1 or Formula 2-2:

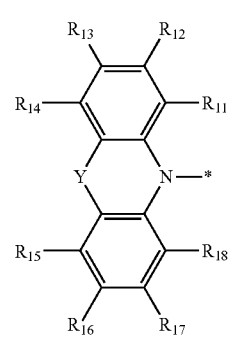

[Formula 2-1]

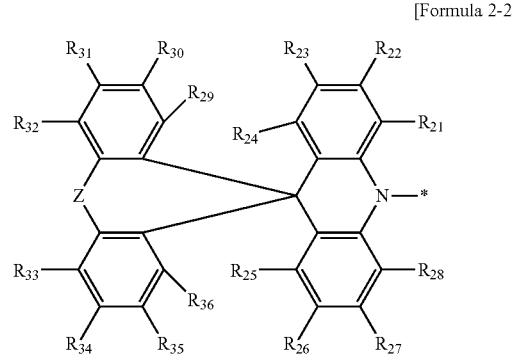

[Formula 2-2]

wherein, in Formula 2-1 and Formula 2-2,

Y is $CR_1R_2$, or $NR_3$,

Z is O, S, $CR_4R_5$, $NR_6$, or $SiR_7R_8$, $R_1$ to $R_5$, $R_7$ and $R_8$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, or $R_1$ and $R_2$, $R_4$ and $R_5$, and $R_7$ and $R_8$ are separate or are combined with each other to form a ring, wherein when forming a ring, $R_1$ and $R_2$ are each independently an alkyl group having 1 to 10 carbon atoms, or an aryl group having 6 to 30 ring carbon atoms, each unsubstituted or substituted with a deuterium atom, a halogen atom, a cyano group, an unsubstituted alkyl group having 1 to 10 carbon atoms, an unsubstituted aryl group having 6 to 30 ring carbon atoms, or an unsubstituted heteroaryl group having 2 to 30 ring carbon atoms, $R_6$ is a hydrogen atom, a deuterium atom, a halogen atom, a cyano group, or a substituted or unsubstituted alkyl group having 1 to 10 carbon atoms, $R_{11}$ to $R_{18}$, and $R_{21}$ to $R_{36}$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and in $R_{11}$ to $R_{18}$, and $R_{21}$ to $R_{36}$, substituents of the substituted or unsubstituted alkyl group having 1 to 10 carbon atoms, the substituted or unsubstituted aryl group having 6 to 30 ring carbon atoms, and the substituted or unsubstituted heteroaryl group having 2 to 30 ring carbon atoms, are each independently a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms, wherein when Y is $CR_1R_2$, at least one of Ra in a number of m, at least one Rb in a number of n, or least one of $R_{13}$ and $R_{16}$ is selected from a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and wherein when Z is $NR_6$, at least one of Ra in a number of m or at least one Rb in a number of n is selected from a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

2. The nitrogen-containing compound as claimed in claim 1, wherein the compound represented by Formula 1 is represented by one of the following Formula 1-1 to Formula 1-3:

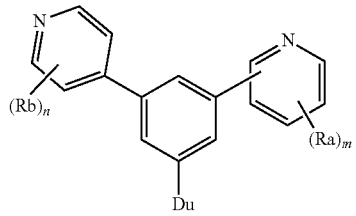

[Formula 1-1]

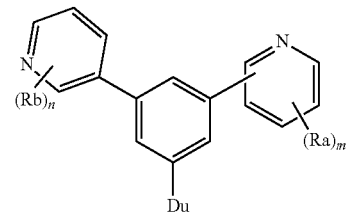

[Formula 1-2]

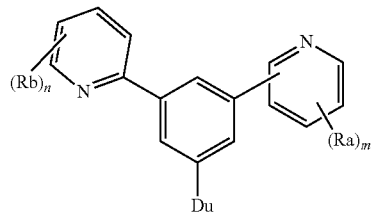

[Formula 1-3]

wherein, in Formula 1-1 to Formula 1-3, Du, Ra, Rb, m and n are defined the same those of Formula 1.

3. The nitrogen-containing compound as claimed in claim 1, wherein the nitrogen-containing compound represented by Formula 1 is a material for emitting thermally activated delayed fluorescence.

4. The nitrogen-containing compound as claimed in claim 1, wherein the nitrogen-containing compound represented by Formula 1 has an absolute value of a difference between a singlet energy level and a triplet energy level of 0.1 eV or less.

5. The nitrogen-containing compound as claimed in claim 1, wherein a triplet energy level of the nitrogen-containing compound represented by Formula 1 is 2.7 eV or more.

6. A nitrogen-containing compound represented by the following Formula 1:

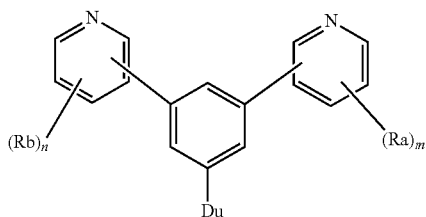

[Formula 1]

wherein, in Formula 1,

Ra and Rb are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, m and n are each independently an integer of 0 to 4, and Du is a group represented by the following Formula 2-1:

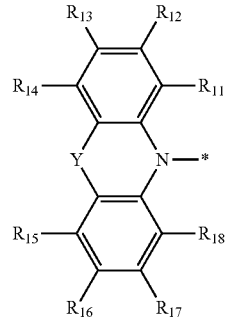

[Formula 2-1]

wherein, in Formula 2-1,

Y is $CR_1R_2$, or $NR_3$, $R_1$ to $R_3$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, or $R_1$ and $R_2$, are separate or are combined with each other to form a ring, wherein when forming a ring, $R_1$ and $R_2$ are each independently a substituted or unsubstituted alkyl group having 1 to 10 carbon atoms, or a substituted or unsubstituted aryl group having 6 to 30 ring carbon atoms, $R_{11}$ to $R_{18}$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and in $R_{11}$ to $R_{18}$ substituents of the substituted or unsubstituted alkyl group having 1 to 10 carbon atoms, the substituted or unsubstituted aryl group having 6 to 30 ring carbon atoms, and the substituted or unsubstituted heteroaryl group having 2 to 30 ring carbon atoms, are each independently a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms, wherein when Y is $CR_1R_2$, at least one of Ra in a number of m, at least one Rb in a number of n, or least one of $R_{13}$ and $R_{16}$ is selected from a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and the group represented by Formula 2-1 is a group represented by one of the following Formula 2a to Formula 2c:

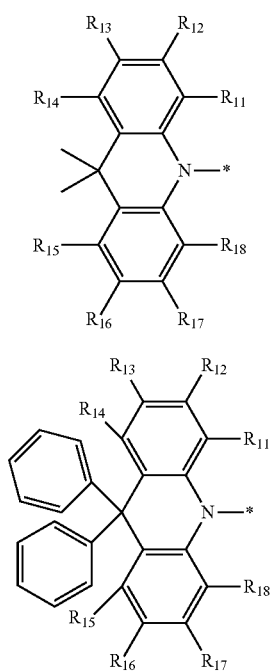

[Formula 2a]

[Formula 2b]

[Formula 2c]

wherein, in Formula 2a to Formula 2c, $R_{11}$ to $R_{18}$ are defined the same as those of Formula 2-1.

7. The nitrogen-containing compound as claimed in claim 1, wherein:

Du is a group represented by Formula 2-2, and the group represented by Formula 2-2 is a group represented by one of the following Formula 2d, Formula 2e and Formula 2g to Formula 2i:

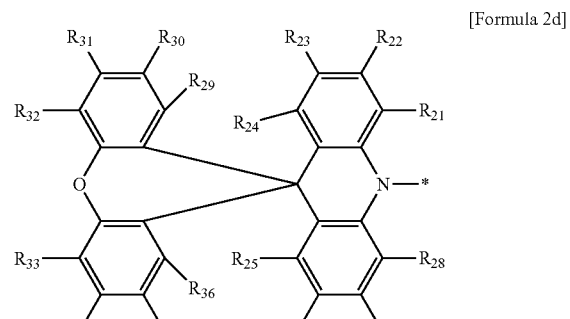

[Formula 2d]

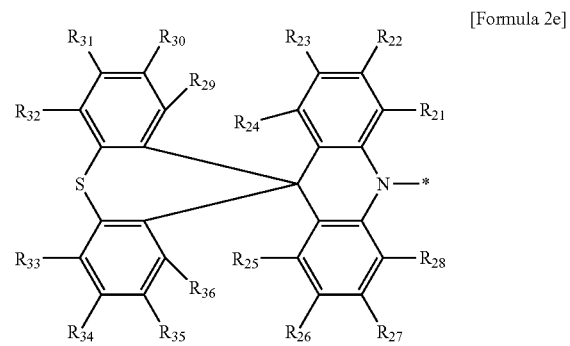

[Formula 2e]

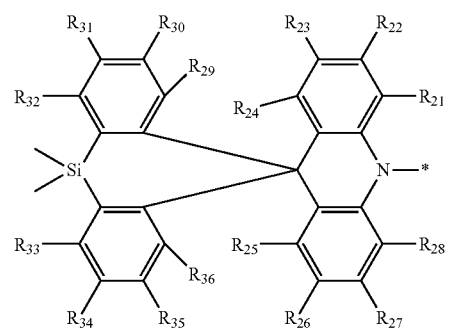

[Formula 2g]

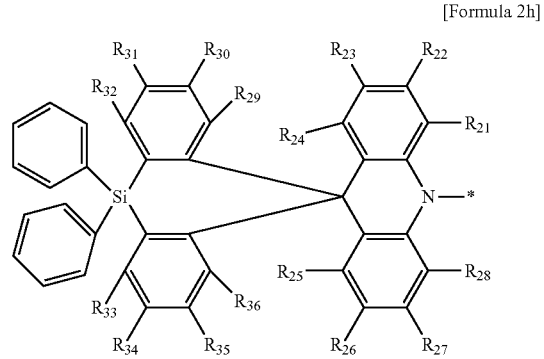

[Formula 2h]

[Formula 2i]

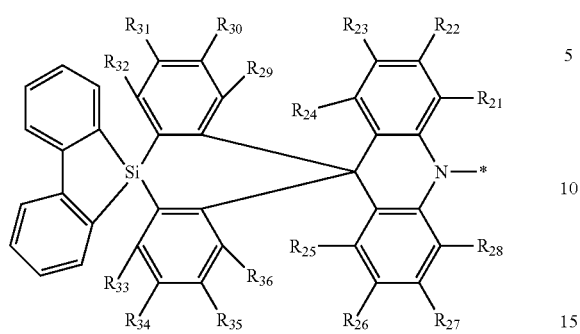

wherein, in Formula 2d, Formula 2e and Formula 2g to Formula 2i, $R_{21}$ to $R_{36}$ are defined the same as those of Formula 2-2.

8. The nitrogen-containing compound as claimed in claim 1, wherein, in Formula 2-1 and Formula 2-2, $R_{11}$ to $R_{18}$, and $R_{21}$ to $R_{36}$ are each independently a hydrogen atom, a methyl group, a t-butyl group, or an unsubstituted phenyl group.

9. The nitrogen-containing compound as claimed in claim 1, wherein the nitrogen-containing compound represented by Formula 1 is a compound of the following Compound Group 1:

[Compound Group 1]

1

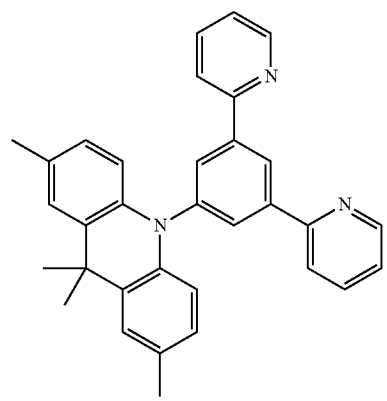

2

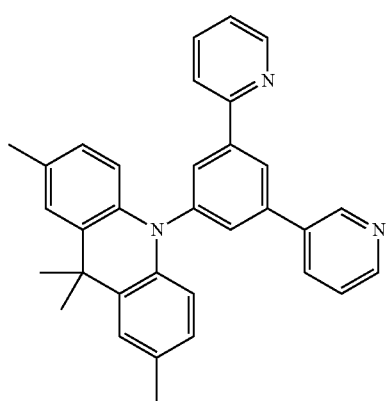

3

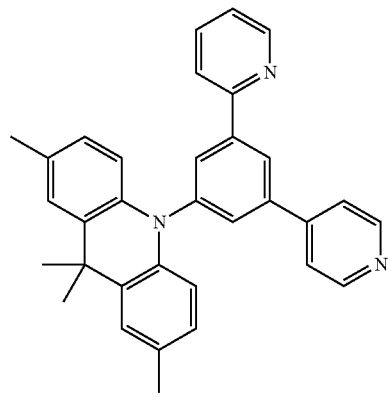

4

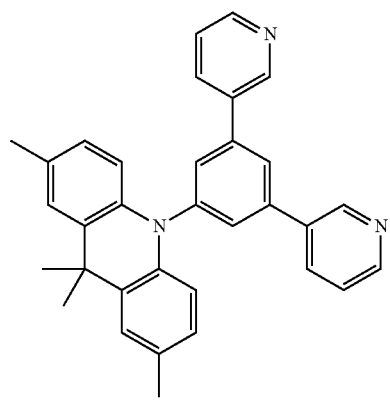

5

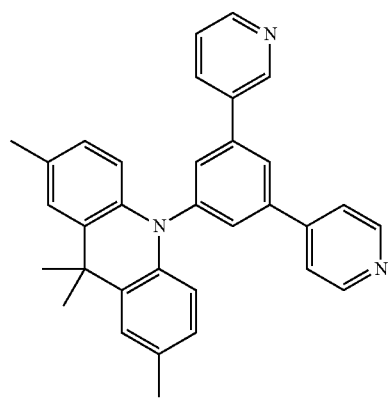

6

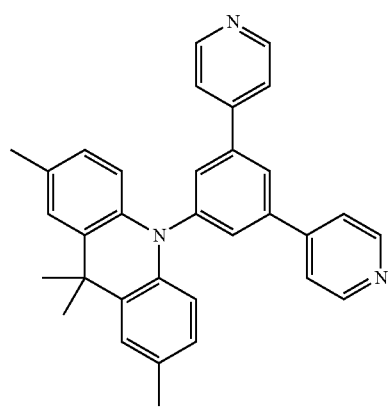

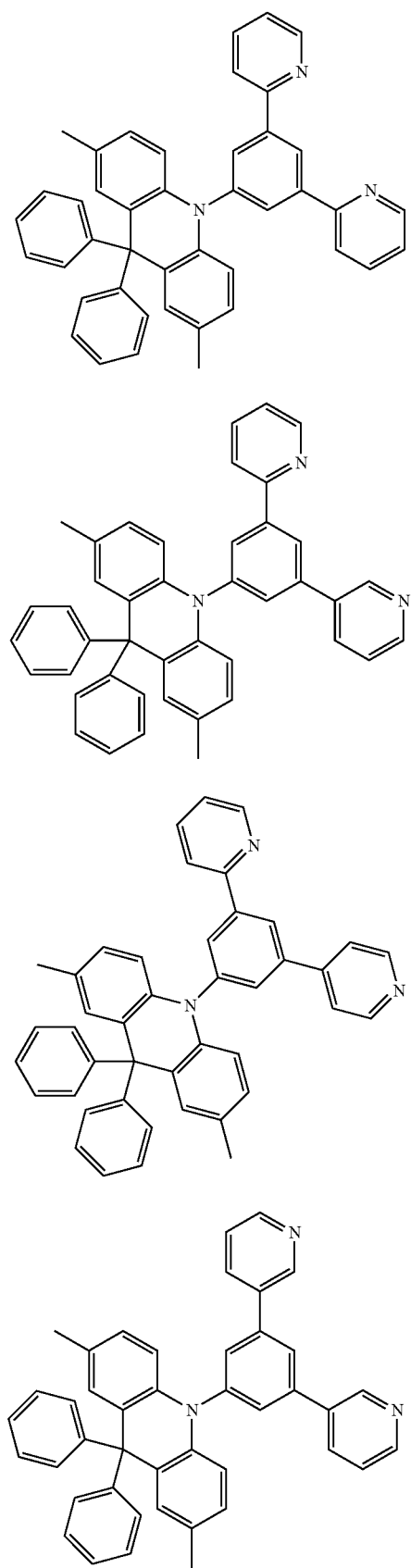
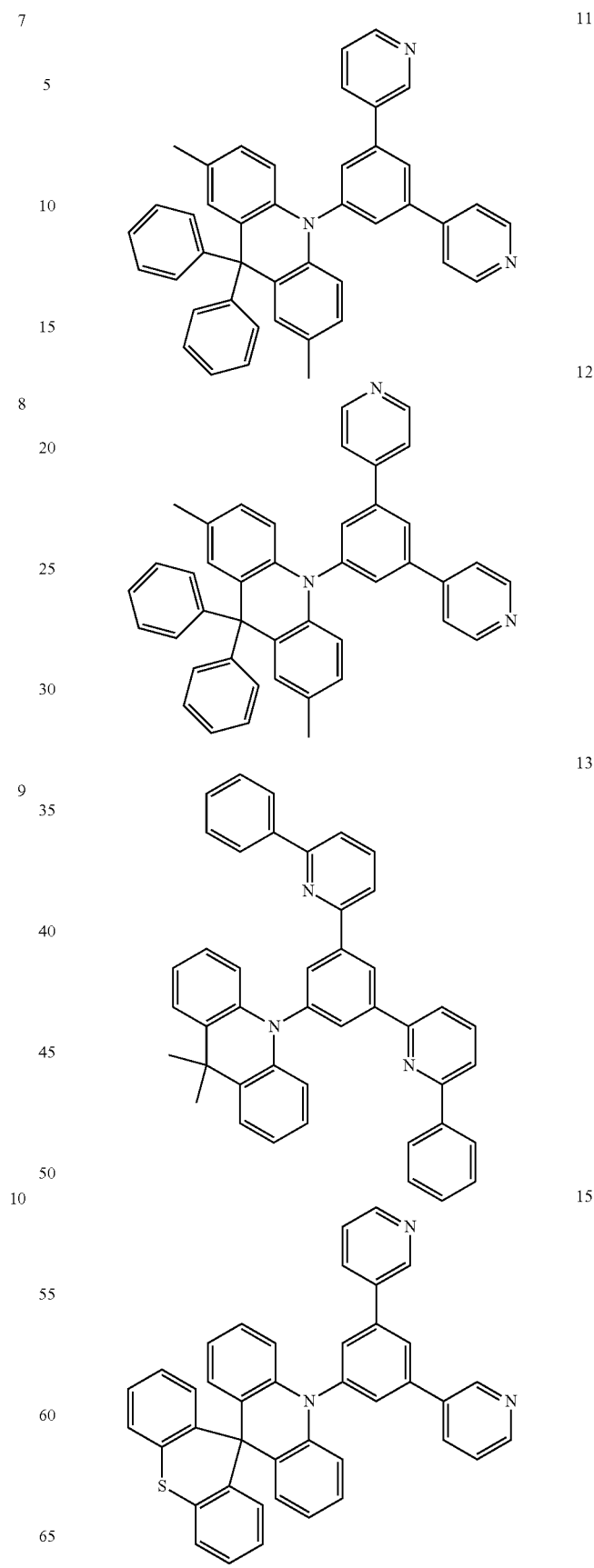

16
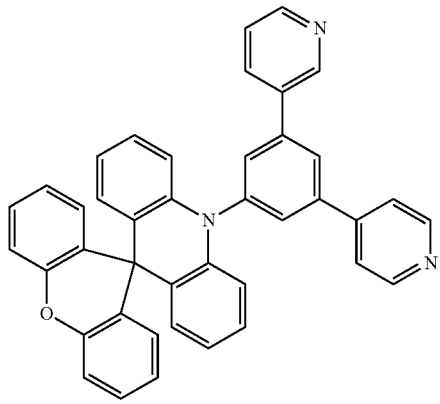
17
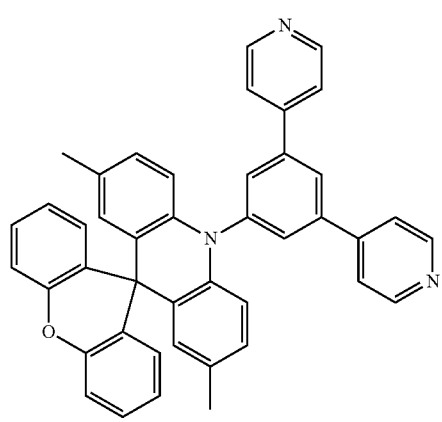
18
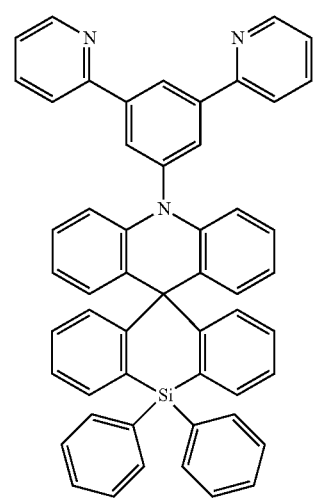
19
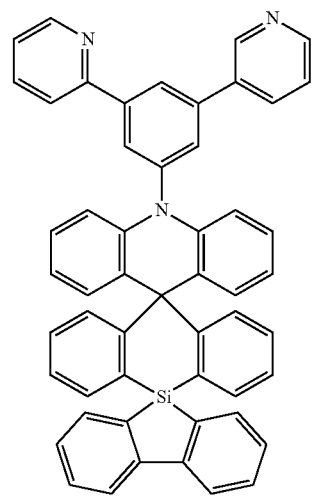
20
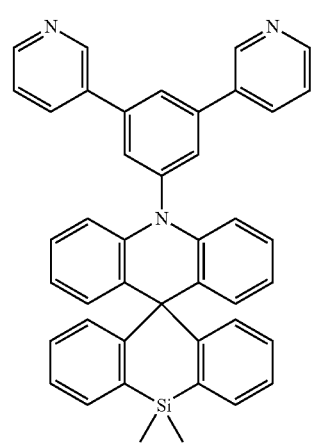
21
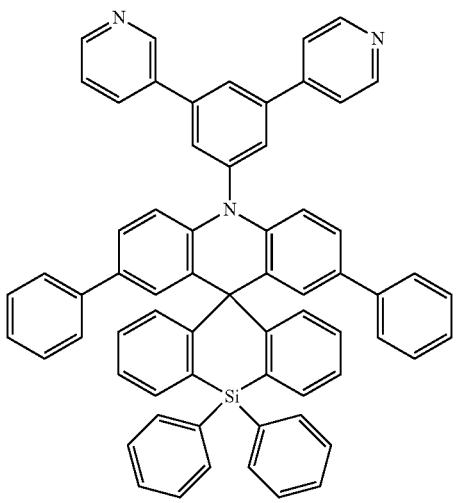

-continued

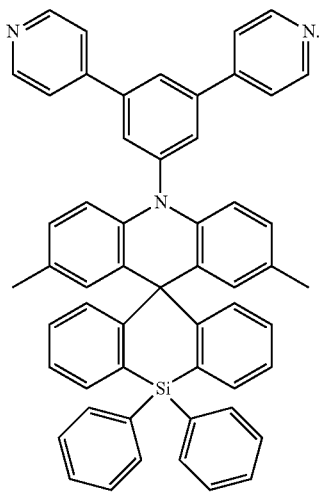

22

10. An organic electroluminescence device, comprising:

a first electrode;

a hole transport region disposed on the first electrode;

an emission layer disposed on the hole transport region;

an electron transport region disposed on the emission layer; and a second electrode disposed on the electron transport region, wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more thereof, a mixture of two or more thereof, or an oxide thereof, wherein the emission layer includes a nitrogen-containing compound represented by the following Formula 1:

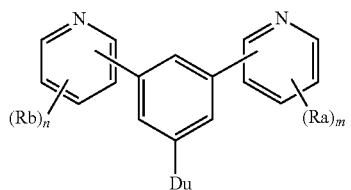

[Formula 1]

wherein, in Formula 1,

Ra and Rb are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, m and n are each independently an integer of 0 to 4, and Du is a group represented by the following Formula 2-1 or Formula 2-2:

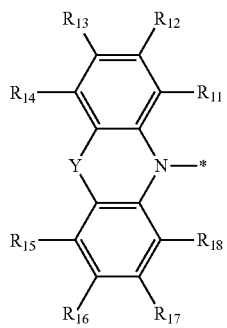

[Formula 2-1]

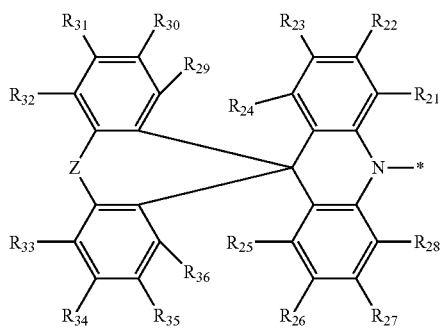

[Formula 2-2]

wherein, in Formula 2-1 and Formula 2-2,

Y is $CR_1R_2$, or $NR_3$,

Z is O, S, $CR_4R_5$, $NR_6$, or $SiR_7R_8$, $R_1$ to $R_5$, $R_7$ and $R_8R_8$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, or $R_1$ and $R_2$, $R_4$ and $R_5$, and $R_7$ and $R_8$ are separate or are combined with each other to form a ring, wherein when forming a ring, $R_1$ and $R_2$, are each independently an alkyl group having 1 to 10 carbon atoms, or an aryl group having 6 to 30 ring carbon atoms, each unsubstituted or substituted with a deuterium atom, a halogen atom, a cyano group, an unsubstituted alkyl group having 1 to 10 carbon atoms, an unsubstituted aryl group having 6 to 30 ring carbon atoms, or an unsubstituted heteroaryl group having 2 to 30 ring carbon atoms, $R_6$ is a hydrogen atom, a deuterium atom, a halogen atom, a cyano group, or a substituted or unsubstituted alkyl group having 1 to 10 carbon atoms, $R_{11}$ to $R_{18}$, and $R_{21}$ to $R_{36}$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and in $R_{11}$ to $R_{18}$, and $R_{21}$ to $R_{36}$, substituents of the substituted or unsubstituted alkyl group having 1 to 10 carbon atoms, the substituted or unsubstituted aryl group having 6 to 30 ring carbon atoms, and the substituted or unsubstituted heteroaryl group having 2 to 30 ring carbon atoms, are each independently a deuterium atom, a halogen atom, a cyano group, an alkyl group having 1 to 10 carbon atoms, an unsubstituted aryl group having 6 to 30 ring carbon atoms, or an unsubstituted heteroaryl group having 2 to 30 ring carbon atoms, wherein when Y is $CR_1R_2$, at least one of Ra in a number of m, at least one Rb in a number of n, or least one of $R_{13}$ and $R_{16}$ is selected from a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and wherein when Z is $NR_6$, at least one of Ra in a number of m or at least one Rb in a number of n is selected from a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

11. The organic electroluminescence device as claimed in claim 10, wherein the emission layer is to emit delayed fluorescence.

12. The organic electroluminescence device as claimed in claim 10, wherein:
the emission layer is a delayed fluorescence emission layer including a host and a dopant, and
the dopant includes the nitrogen-containing compound represented by Formula 1.

13. The organic electroluminescence device as claimed in claim 10, wherein the emission layer is a thermally activated delayed fluorescence emission layer emitting blue light.

14. The organic electroluminescence device as claimed in claim 10, wherein the compound represented by Formula 1 is represented by one of the following Formula 1-1 to Formula 1-3:

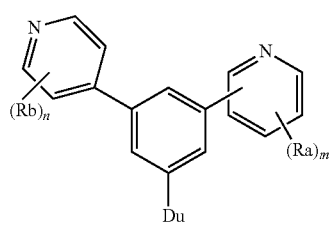
[Formula 1-1]

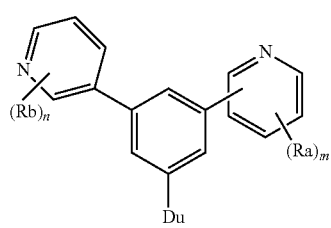
[Formula 1-2]

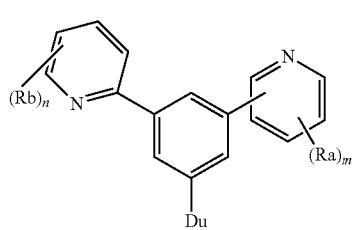
[Formula 1-3]

wherein, in Formula 1-1 to Formula 1-3, Du, Ra, Rb, m and n are defined the same those of Formula 1.

15. The organic electroluminescence device as claimed in claim 10, wherein Du of Formula 1 is a group represented by one of the following to Formula 2a to Formula 2e and Formula 2g to Formula 2i:

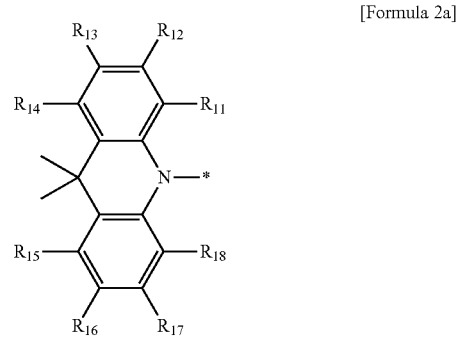
[Formula 2a]

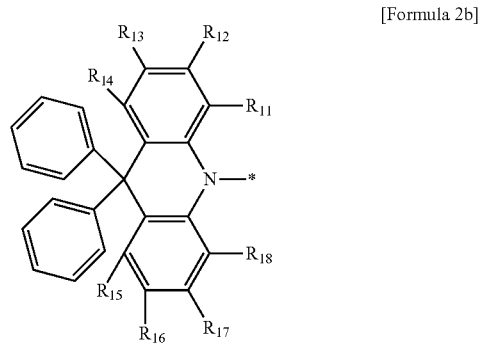
[Formula 2b]

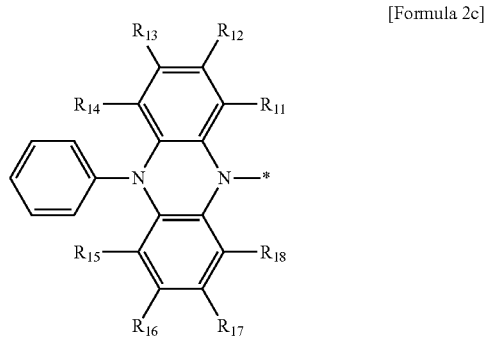
[Formula 2c]

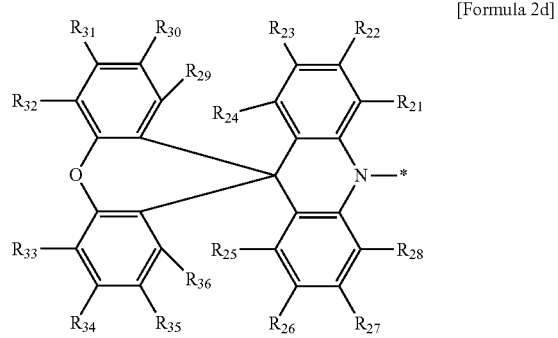
[Formula 2d]

[Formula 2e]
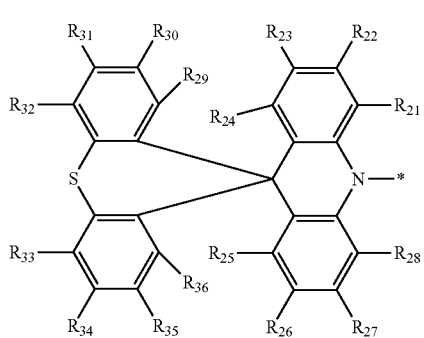
[Formula 2g]
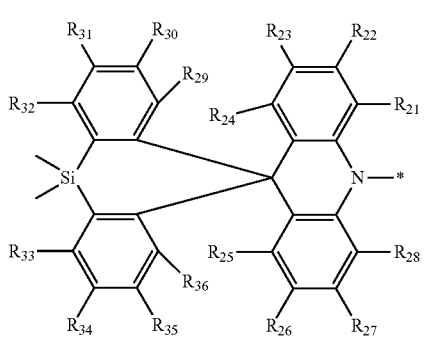
[Formula 2h]
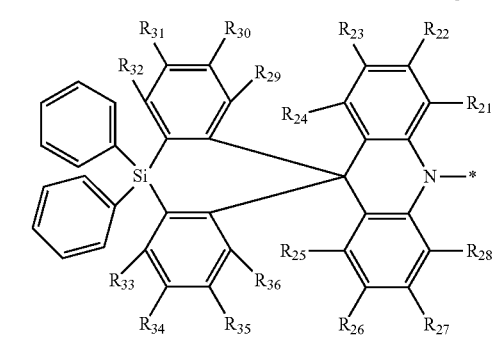
[Formula 2i]
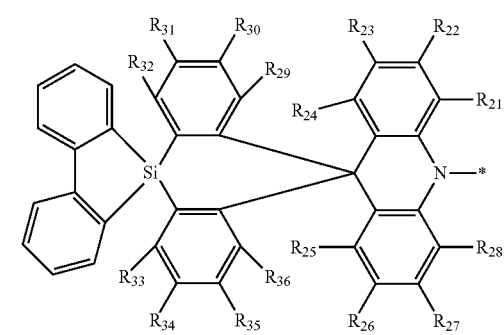
wherein, in Formula 2a to Formula 2i, $R_{11}$ to $R_{18}$, and $R_{21}$ to $R_{36}$ are defined the same as those of Formula 2-1 and Formula 2-2.
16. The organic electroluminescence device as claimed in claim 10, wherein the nitrogen-containing compound represented by Formula 1 is a compound of the following Compound Group 1:
[Compound Group 1]
1
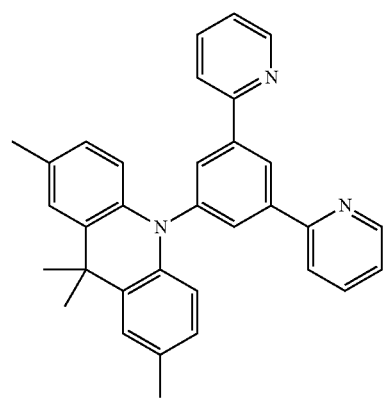
2
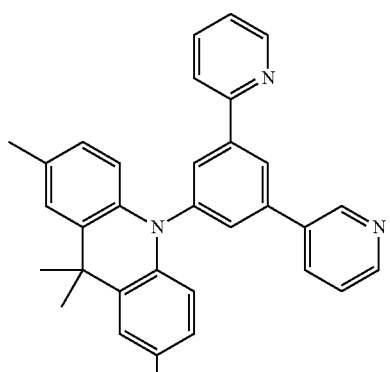
3
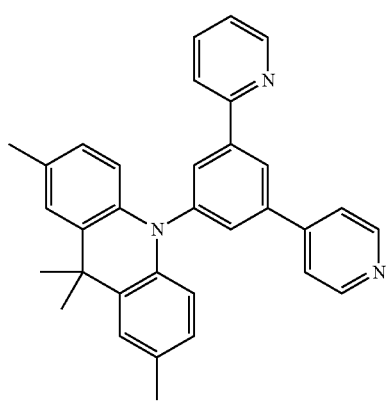
4
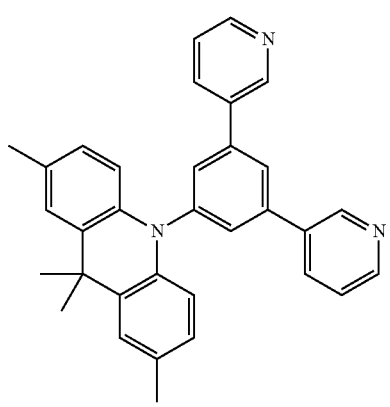

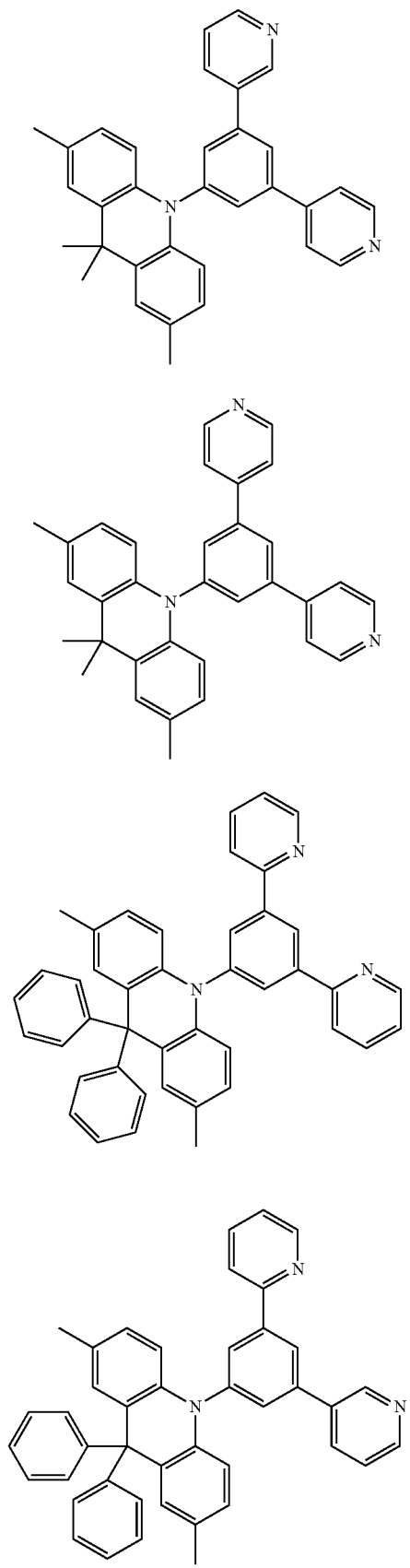
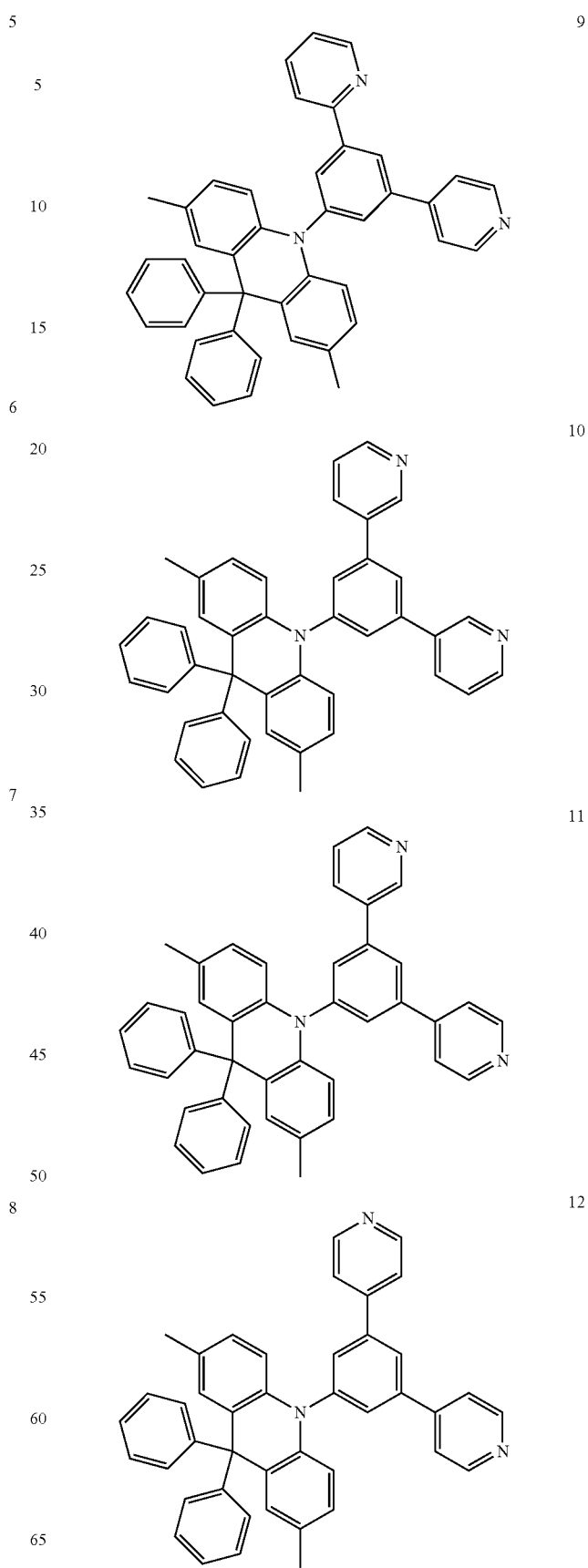

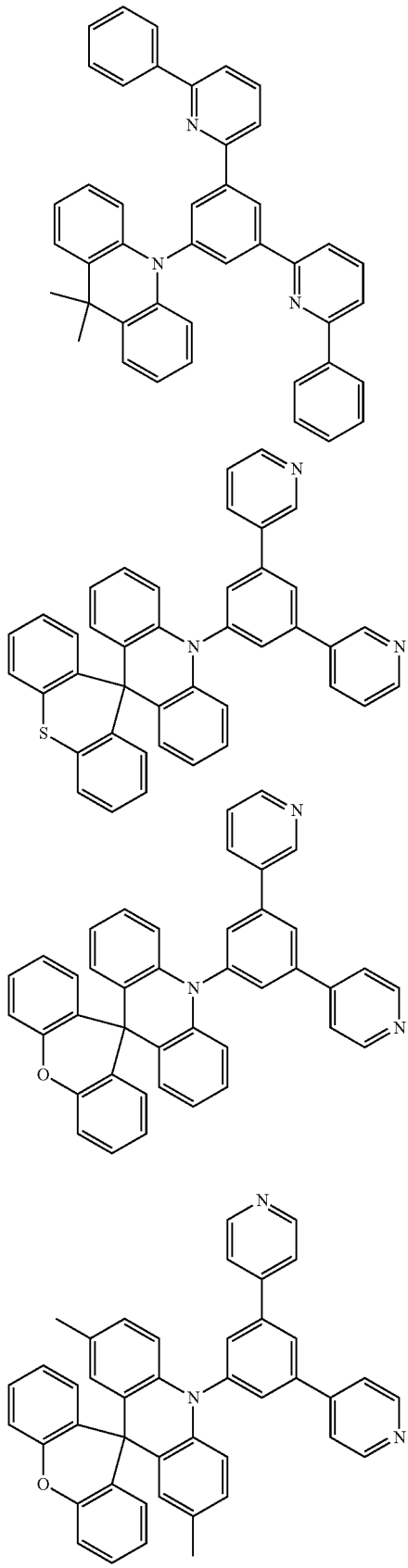
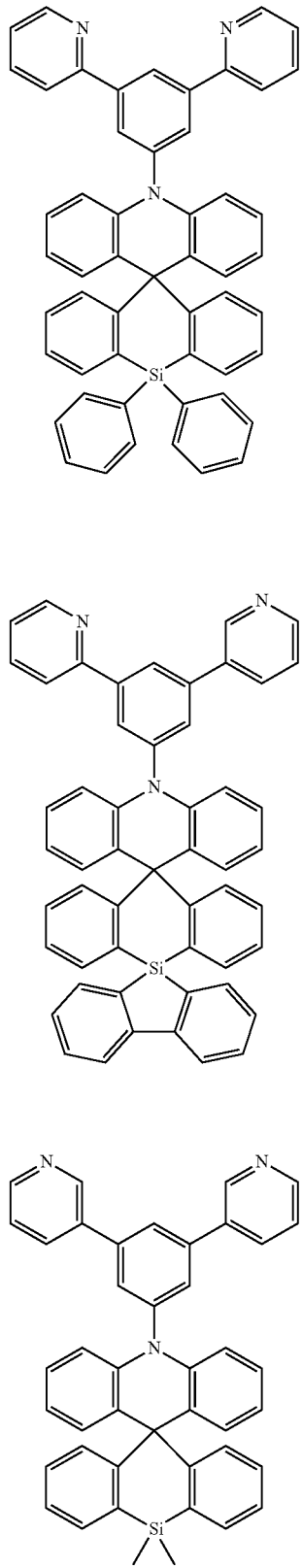

91
-continued
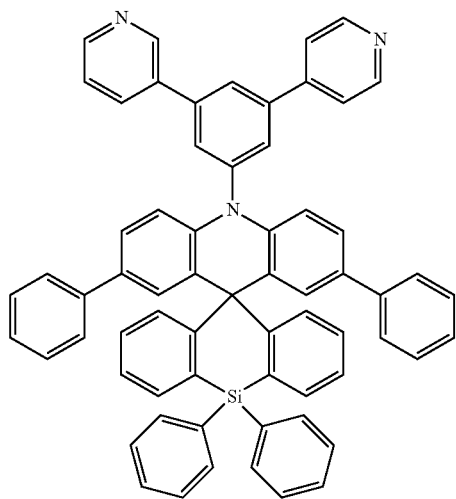
92
-continued
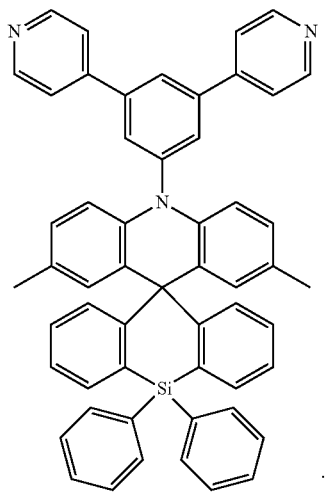
* * * * *